US011350819B2

United States Patent
Tanaka et al.

(10) Patent No.: US 11,350,819 B2
(45) Date of Patent: Jun. 7, 2022

(54) ENDOSCOPE SYSTEM HAVING FAILURE DETECTING CIRCUIT TO DETECT FAILURE OF AN ENDOSCOPE

(71) Applicant: OLYMPUS CORPORATION, Tokyo (JP)

(72) Inventors: Yoshinori Tanaka, Hino (JP); Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 795 days.

(21) Appl. No.: 16/108,419

(22) Filed: Aug. 22, 2018

(65) Prior Publication Data
US 2018/0353061 A1 Dec. 13, 2018

Related U.S. Application Data

(63) Continuation of application No. PCT/JP2016/055679, filed on Feb. 25, 2016.

(51) Int. Cl.
*A61B 1/06* (2006.01)
*A61B 1/045* (2006.01)
(Continued)

(52) U.S. Cl.
CPC ........ *A61B 1/0676* (2013.01); *A61B 1/00006* (2013.01); *A61B 1/00057* (2013.01);
(Continued)

(58) Field of Classification Search
None
See application file for complete search history.

(56) References Cited

U.S. PATENT DOCUMENTS 5,034,010 A * 7/1991 Kittrell ................ A61B 5/0084
606/15
5,408,263 A * 4/1995 Kikuchi ............. A61B 1/00059
348/223.1
(Continued)

FOREIGN PATENT DOCUMENTS

JP 2007117583 A 5/2007
JP 4732783 B2 7/2011
(Continued)

OTHER PUBLICATIONS

Machine English Translation of JP2007117583A, Enomoto Takayuki, May 17, 2007.*
(Continued)

*Primary Examiner* — Michael J Carey
*Assistant Examiner* — Minqiao Huang
(74) *Attorney, Agent, or Firm* — Scully, Scott, Murphy & Presser, P.C.

(57) ABSTRACT

An endoscope system includes an endoscope including a control section, an insertion section, and a light guide member, a light source configured to emit light guided by the light guide member, a failure-cause detecting circuit configured to detect a pre-failure state that causes a failure of the endoscope, and a light source controller configured to control an output of the light source based on a detection result of the failure-cause detecting circuit. The failure-cause detecting circuit includes a cause predicting circuit configured to detect a second pre-failure state in which it is predicted that the endoscope reaches a first pre-failure state that directly causes the failure of the endoscope. The light source controller controls the output of the light source based on a detection result of the cause predicting circuit.

18 Claims, 16 Drawing Sheets

(51) Int. Cl.
*A61B 1/00* (2006.01)
*A61B 1/12* (2006.01)
*A61B 1/05* (2006.01)
*A61B 1/07* (2006.01)
*G02B 23/24* (2006.01)

(52) U.S. Cl.
CPC ............... *A61B 1/045* (2013.01); *A61B 1/05* (2013.01); *A61B 1/0653* (2013.01); *A61B 1/07* (2013.01); *A61B 1/128* (2013.01); *G02B 23/2469* (2013.01); *A61B 1/00096* (2013.01)

(56) References Cited

U.S. PATENT DOCUMENTS

| | | | | |
|---|---|---|---|---|
| 9,445,477 B2* | 9/2016 | Yamamoto | ............. | H05B 45/50 |
| 2002/0007111 A1* | 1/2002 | Deckert | ............. | G02B 23/2469 |
| | | | | 600/177 |
| 2004/0106849 A1* | 6/2004 | Cho | ................... | A61B 5/14539 |
| | | | | 600/101 |
| 2009/0225156 A1* | 9/2009 | Akiyama | ........... | A61B 1/00096 |
| | | | | 348/68 |
| 2011/0130632 A1* | 6/2011 | McGrail | ................ | A61B 1/267 |
| | | | | 600/188 |
| 2012/0167882 A1* | 7/2012 | Wood | ..................... | A61B 1/128 |
| | | | | 128/204.17 |
| 2013/0169775 A1* | 7/2013 | Ono | ....................... | A61B 1/128 |
| | | | | 348/68 |
| 2013/0342110 A1* | 12/2013 | Yamamoto | ........... | G02B 6/0008 |
| | | | | 315/151 |
| 2014/0221740 A1* | 8/2014 | Kawula | .................... | A61B 1/07 |
| | | | | 600/109 |
| 2014/0340496 A1* | 11/2014 | Okawa | .................. | H04N 5/243 |
| | | | | 348/65 |
| 2015/0091447 A1* | 4/2015 | Kubo | .................... | A61B 1/045 |
| | | | | 315/153 |

FOREIGN PATENT DOCUMENTS

| | | |
|---|---|---|
| JP | 2011239989 A | 12/2011 |
| JP | 2012050509 A | 3/2012 |
| JP | 2014223551 A | 12/2014 |

OTHER PUBLICATIONS

International Search Report dated May 24, 2016 issued in PCT/JP2016/055679.
English translation of International Preliminary Report on Patentability dated Sep. 7, 2018 together with the Written Opinion received in related International Application No. PCT/JP2016/055679.
Japanese Office Action dated May 7, 2019 in Japanese Patent Application No. 2018-501507.

* cited by examiner

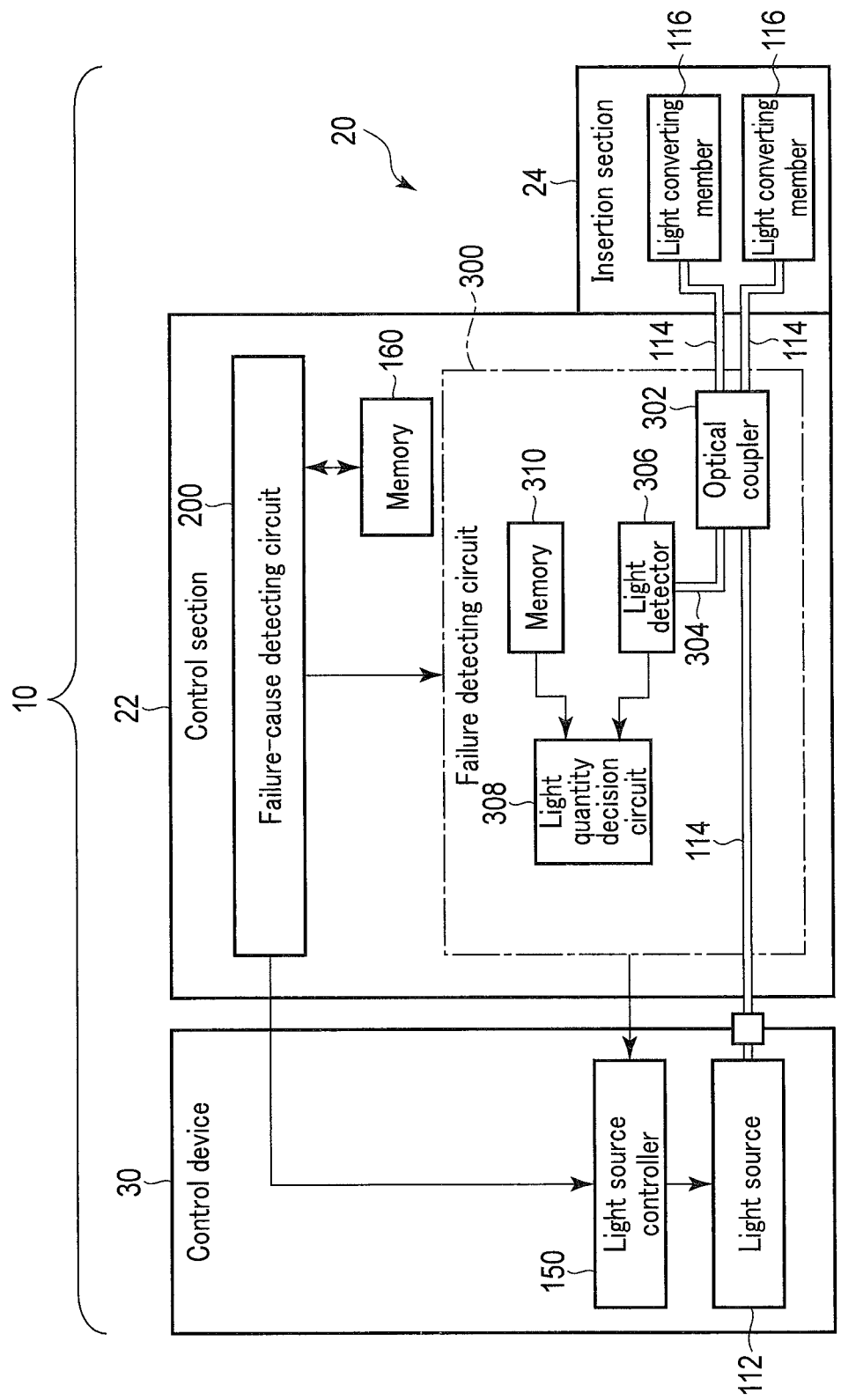
F I G. 11

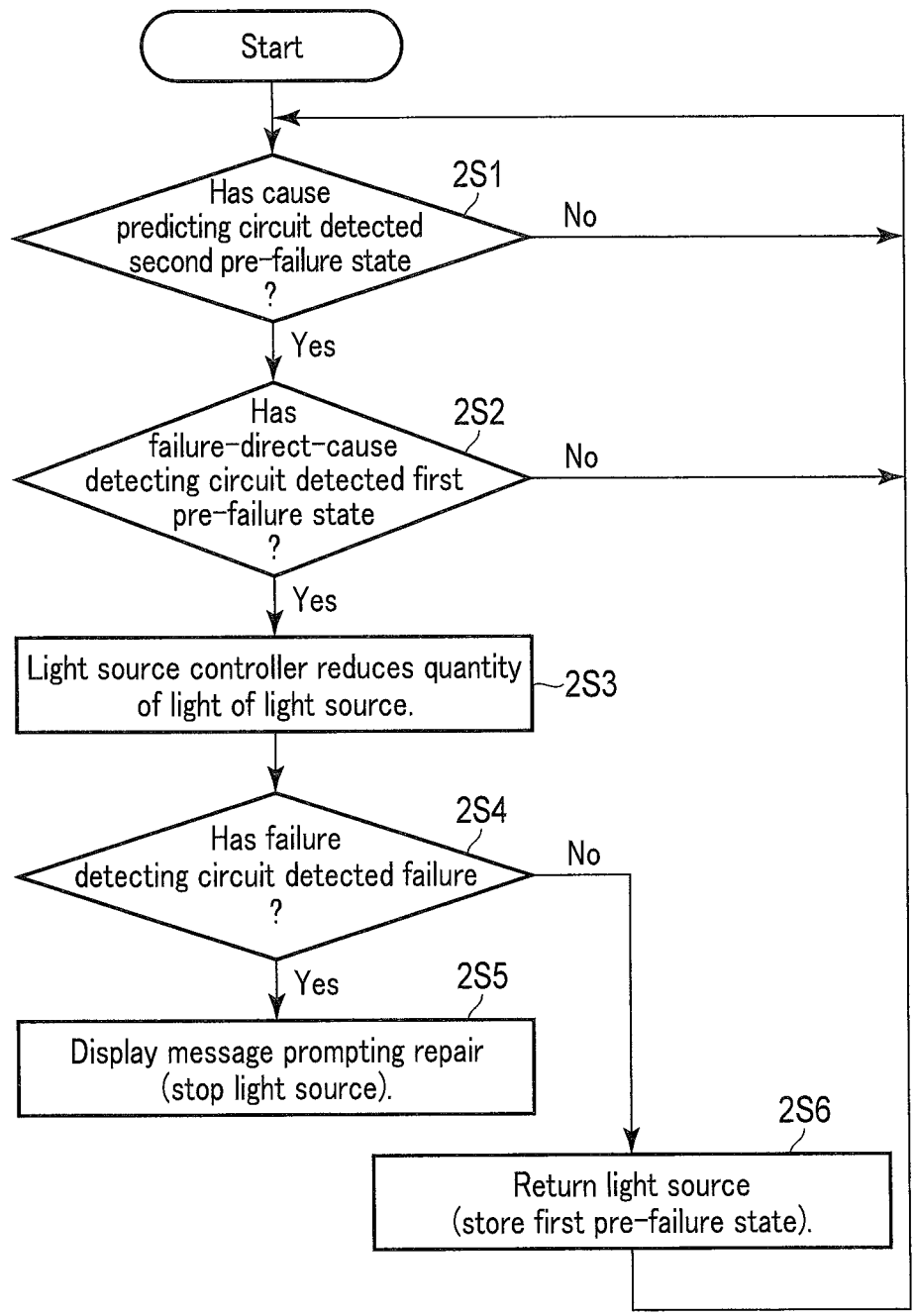
F I G. 12

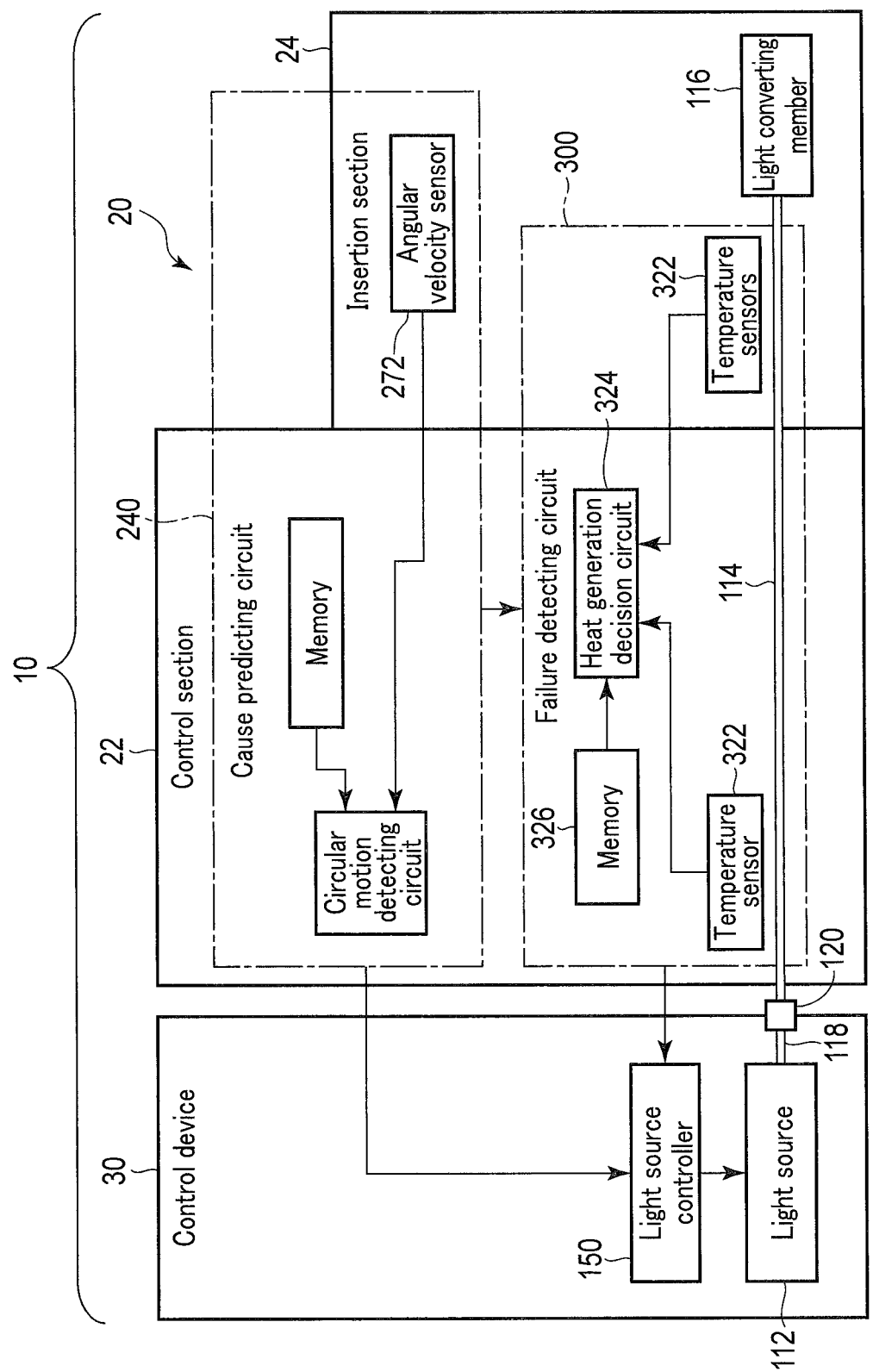
F I G. 13

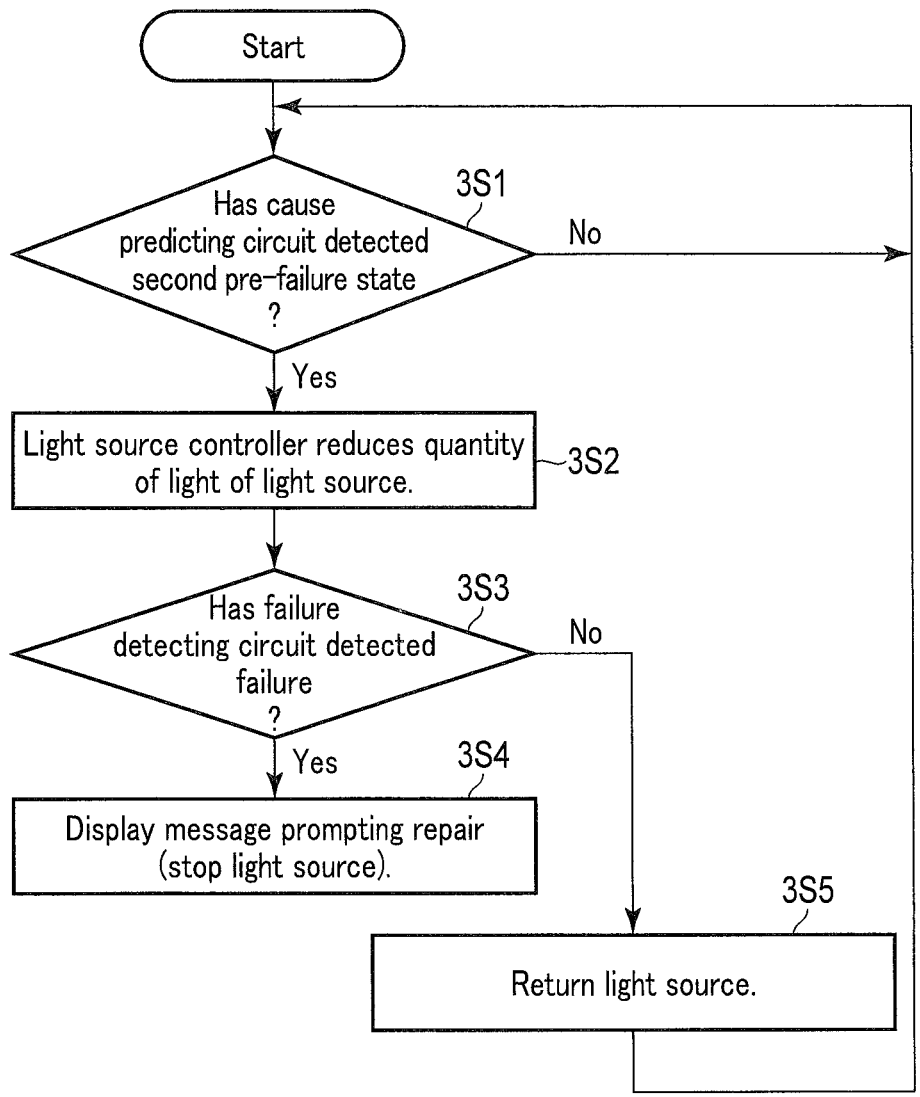
F I G. 14

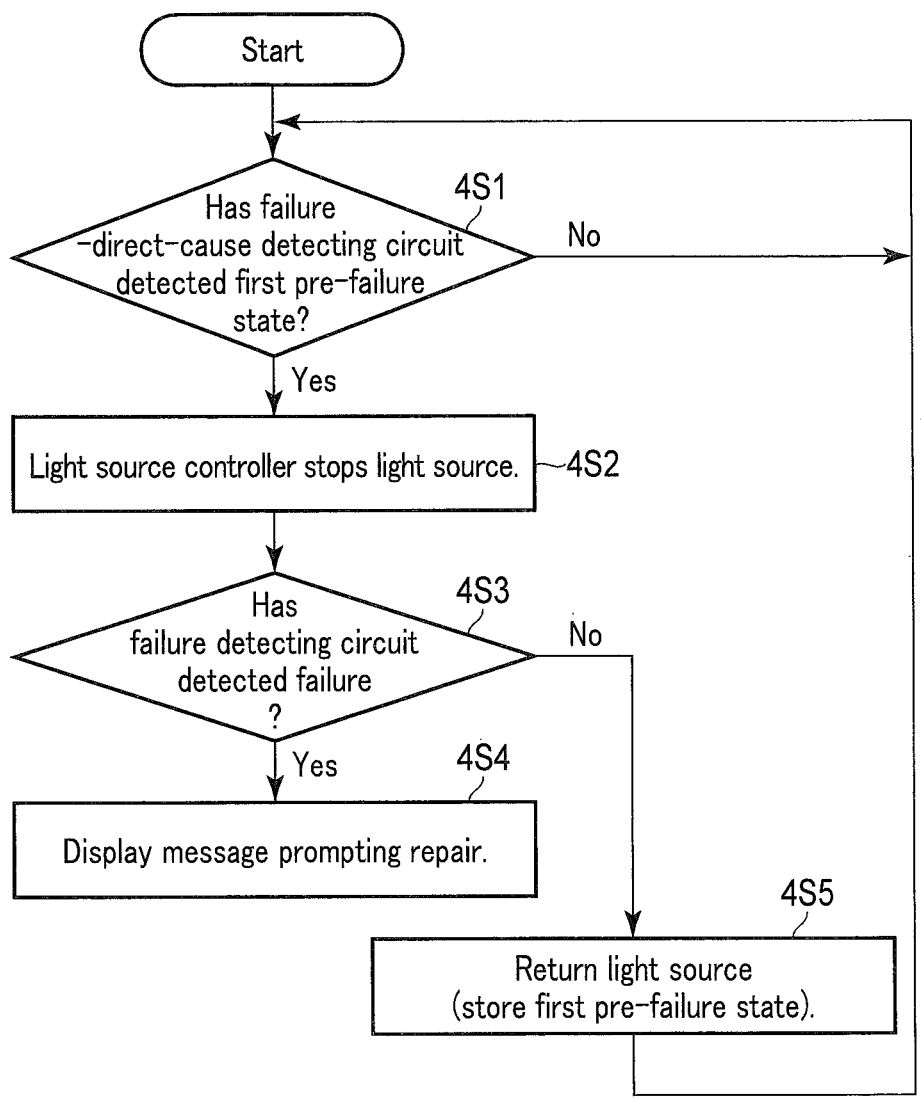
F I G. 16

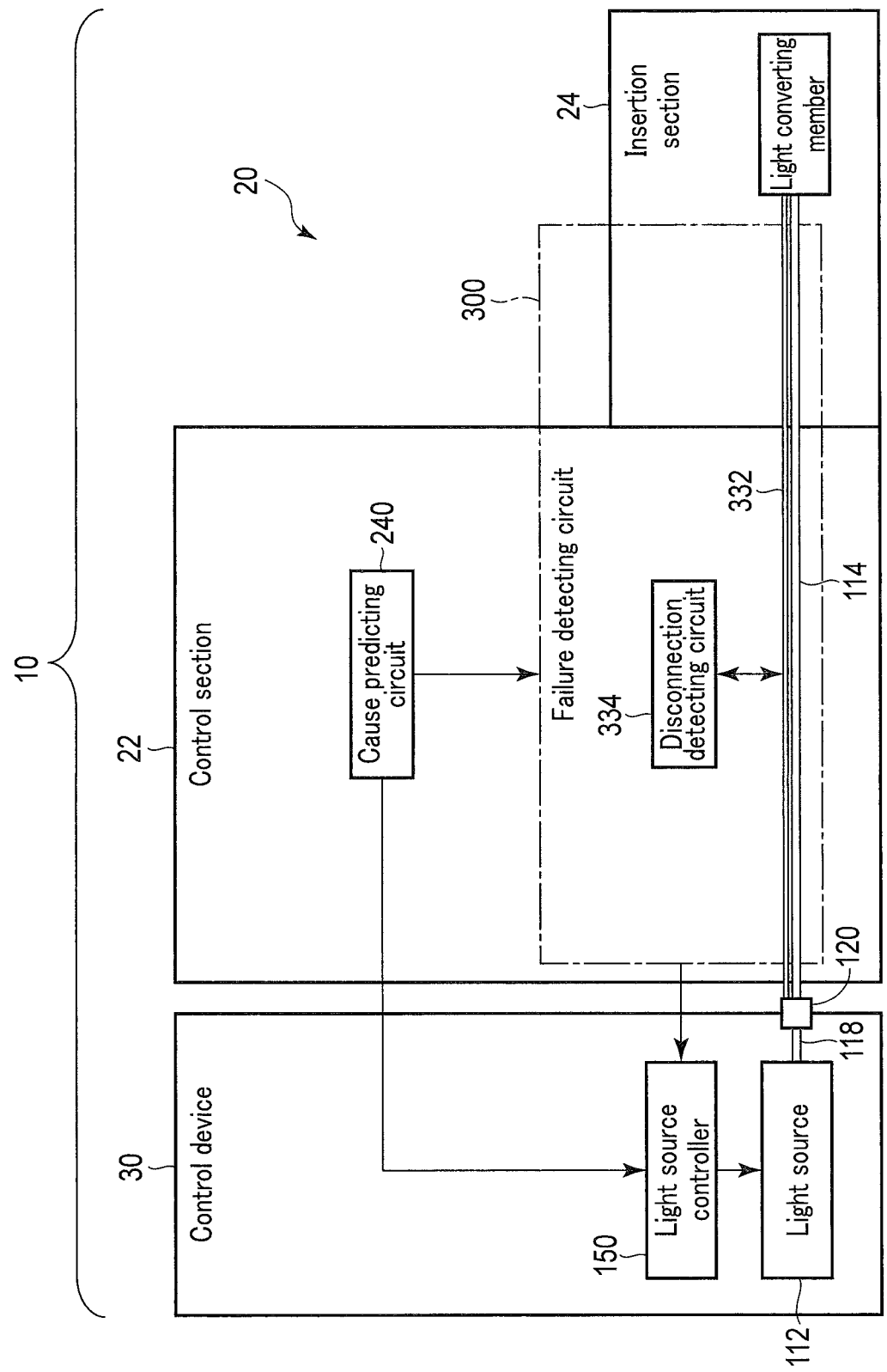
F I G. 17

ENDOSCOPE SYSTEM HAVING FAILURE DETECTING CIRCUIT TO DETECT FAILURE OF AN ENDOSCOPE

CROSS-REFERENCE TO RELATED APPLICATIONS

This application is a Continuation Application of PCT Application No. PCT/JP2016/055679, filed Feb. 25, 2016, the entire contents of which are incorporated herein by reference.

BACKGROUND OF THE INVENTION

1. Field of the Invention

The present invention relates to an endoscope system.

2. Description of the Related Art

For example, Japanese Patent No. 4732783 discloses an illumination apparatus for an endoscope capable of outputting illuminating light with uneven color without raising a temperature of an insertion section by including a light guide formed of an optical fiber, a fluorescent substance disposed at a tip end side of the light guide, a semiconductor laser light source outputting excitation light to excite the fluorescent substance, and a converging lens to converge the excitation light to a rear end of the light guide.

BRIEF SUMMARY OF THE INVENTION

An endoscope system includes an endoscope including a control section, an insertion section, and a light guide member, a light source configured to emit light guided by the light guide member, a failure-cause detecting circuit configured to detect a pre-failure state that causes a failure of the endoscope, and a light source controller configured to control an output of the light source based on a detection result of the failure-cause detecting circuit. The failure-cause detecting circuit includes a cause predicting circuit configured to detect a second pre-failure state in which it is predicted that the endoscope reaches a first pre-failure state that directly causes the failure of the endoscope. The light source controller controls the output of the light source based on a detection result of the cause predicting circuit.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 11 shows a configuration example of a failure detecting circuit shown in FIG. 10;

FIG. 12 shows an overall flow of a corresponding process of a case in which an endoscope of the endoscope system according to the second embodiment falls down and then collides with a floor;

FIG. 13 shows function blocks of an endoscope system according to a third embodiment;

FIG. 14 shows an overall flow of a corresponding process of a case in which a distal end of an insertion section of an endoscope of the endoscope system shown in FIG. 13 performs a circular motion;

FIG. 16 shows an overall flow of a corresponding process of a case in which an endoscope of the endoscope system shown in FIG. 15 reaches a first pre-failure state;

FIG. 17 shows function blocks of an endoscope system according to a fifth embodiment.

DETAILED DESCRIPTION OF THE INVENTION

First Embodiment (Configuration)

[Endoscope System 10]

Figure 1:
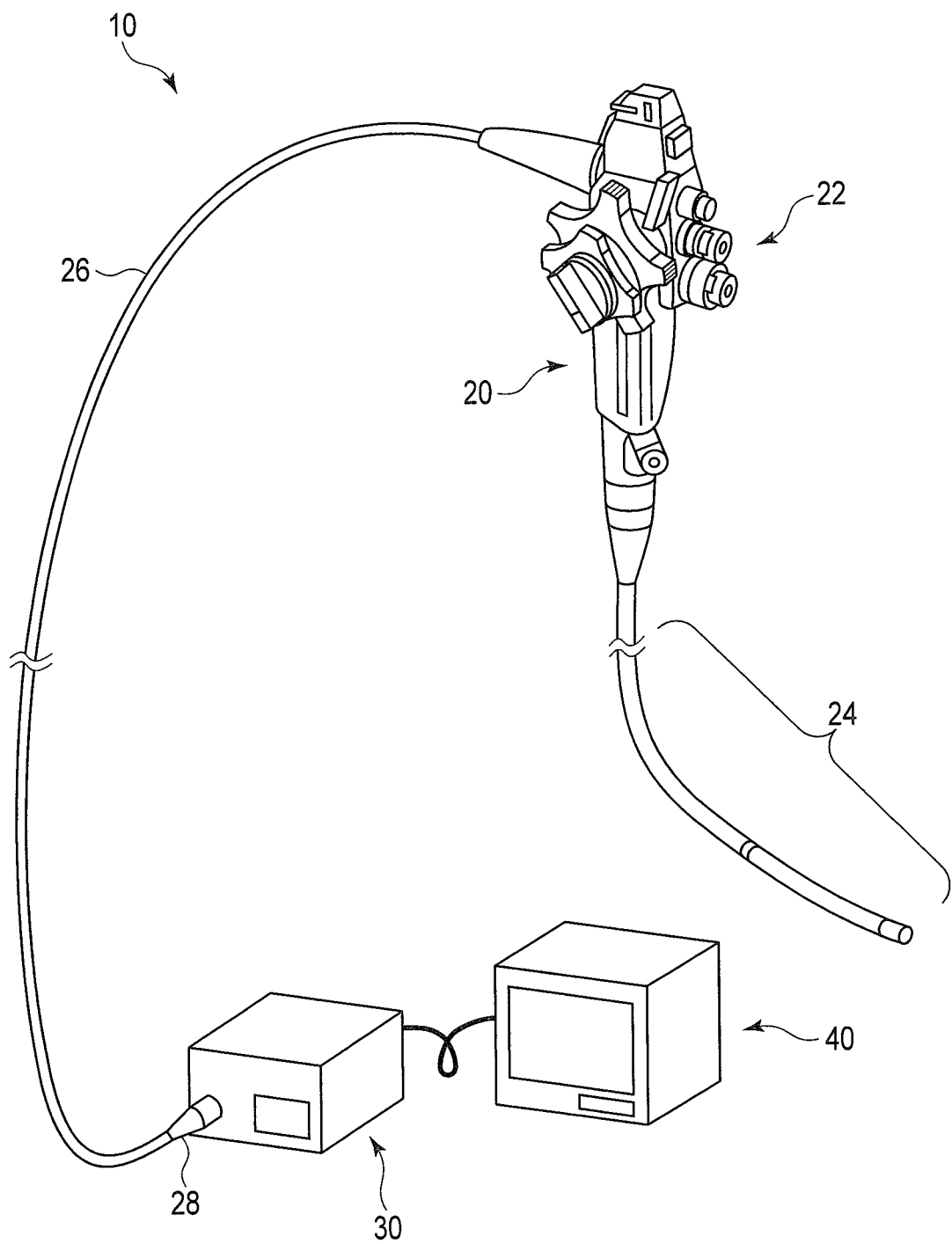
FIG. 1 shows an endoscope system according to a first embodiment.

FIG. 1 shows an endoscope system 10 according to the present embodiment. Such an endoscope system 10 is provided in, for example, an examination room, an operating room, or the like. The endoscope system 10 includes an endoscope 20 configured to image an observation object, a control device 30 configured to perform a processing, etc. of an image imaged by the endoscope 20, and a monitor 40 configured to display the image imaged by the endoscope 20. The observation object is an affect part, a lesion part, or the like in a tube part such as a lumen of a patient.

The endoscope 20 serves as, for example, an insertion device to be inserted into the tube part. The endoscope 20 may be a direct-view endoscope or a side-view endoscope.

The endoscope 20 according to the present embodiment is described as, for example, a medical endoscope 20, but is not limited thereto. The endoscope 20 may be an industrial endoscope to be inserted into a tube part of an industrial product such as a pipe or may be an insertion instrument such as a catheter having only an illuminator.

The endoscope 20 includes a hollow elongated insertion section 24 to be inserted into the tube part, and a control section 22, connected to a proximal end of the insertion section 24, for controlling the endoscope 20.

The endoscope 20 is directly connected to the control device 30 through a universal cord 26. The universal cord 26 includes a connector 28 that is attachable to and detachable from the control device 30. The connector 28 serves as an interface of data transmitted and received between the endoscope 20 and the control device 30.

Figure 2:
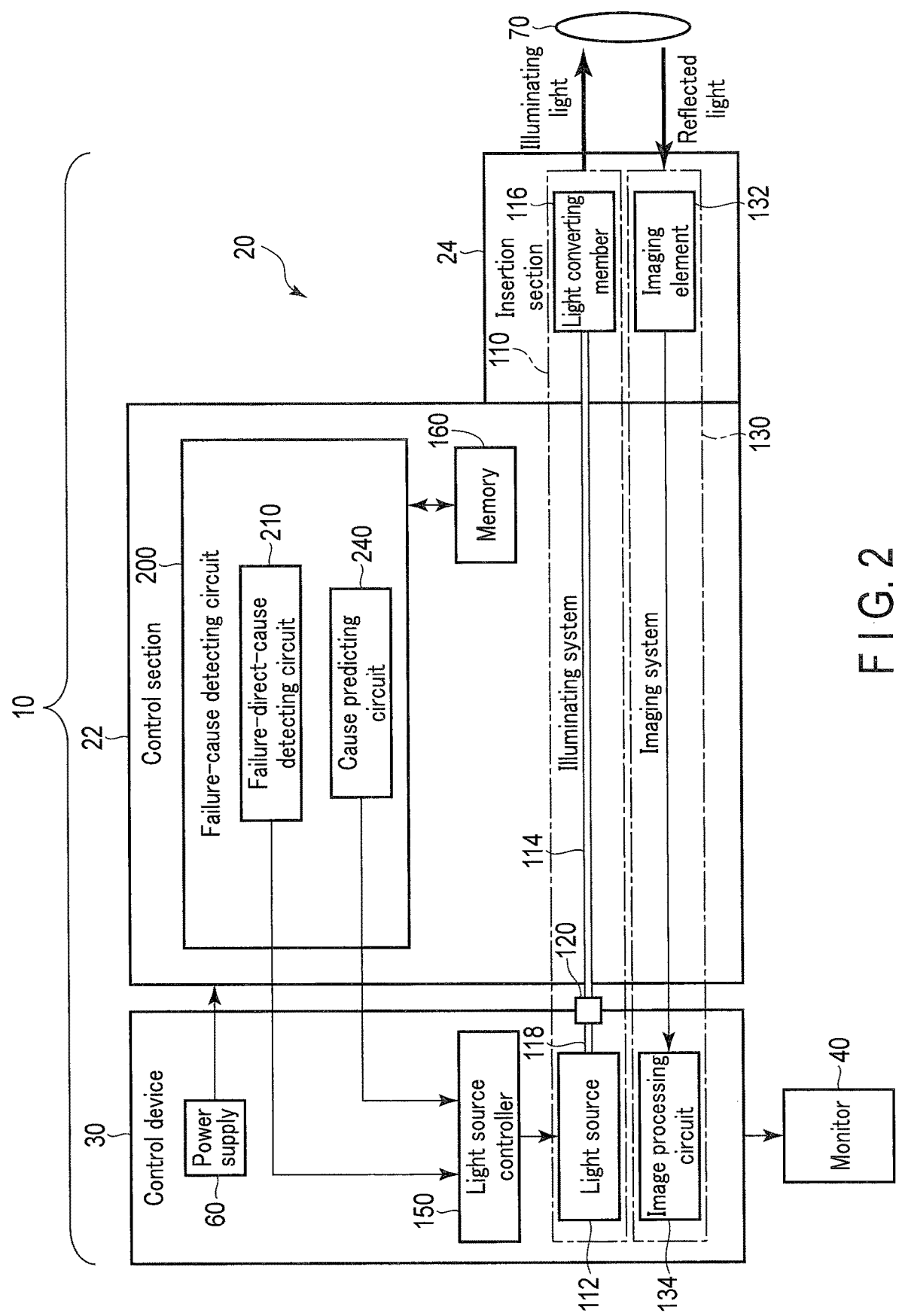
FIG. 2 shows function blocks of the endoscope system shown in FIG. 1.

FIG. 2 shows function blocks of the endoscope system 10 shown in FIG. 1. As shown in FIG. 2, the endoscope system 10 includes an illuminating system 110 for illuminating an observation object 70 and an imaging system 130 for imaging the observation object 70.

The illuminating system 110 includes a light source 112, optical fibers 118 and 114, which are light guide members configured to guide light emitted from the light source 112, an optical connector 120 configured to optically connect the optical fibers 118 and 114 to each other, and a light converting member 116 configured to optically convert the light guided by the optical fiber 114 into illuminating light. The light source 112 and the optical fiber 118 are disposed in the control device 30. The optical fiber 114 extends through the insertion section 24, the control section 22, and the universal cord 26. The optical connector 120 is disposed in the connector 28 of the universal cord 26. The light converting member 116 is disposed at a distal end of the insertion section 24.

The imaging system 130 includes an imaging element 132 configured to photoelectrically convert reflected light from the observation object 70 and an image processing circuit 134 configured to process an image signal output from the imaging element 132. The imaging element 132 is disposed at the distal end of the insertion section 24. The image processing circuit 134 is disposed in the control device 30.

The endoscope 20 includes a failure-cause detecting circuit 200 configured to detect a pre-failure state that causes a failure of the endoscope. The failure-cause detecting circuit 200 includes a failure-direct-cause detecting circuit 210 configured to detect a first pre-failure state that directly causes the failure of the endoscope 20 and a cause predicting circuit 240 configured to detect a second pre-failure state in which it is predicted that the endoscope 20 reaches the first pre-failure state.

The endoscope system also includes a memory 160, which is a recording section configured to store information on a detection result of the failure-cause detecting circuit 200. For example, the memory 160 is disposed inside the endoscope 20, for example, inside the control section 22. The memory 160 is not limited thereto, but may be disposed in the control device 30.

The control device 30 includes a light source controller 150 configured to control an output of the light source 112 based on the detection result of the failure-cause detecting circuit 200. The control device 30 also includes a power supply 60 for driving the control device 30 itself and the endoscope 20.

Figure 3:
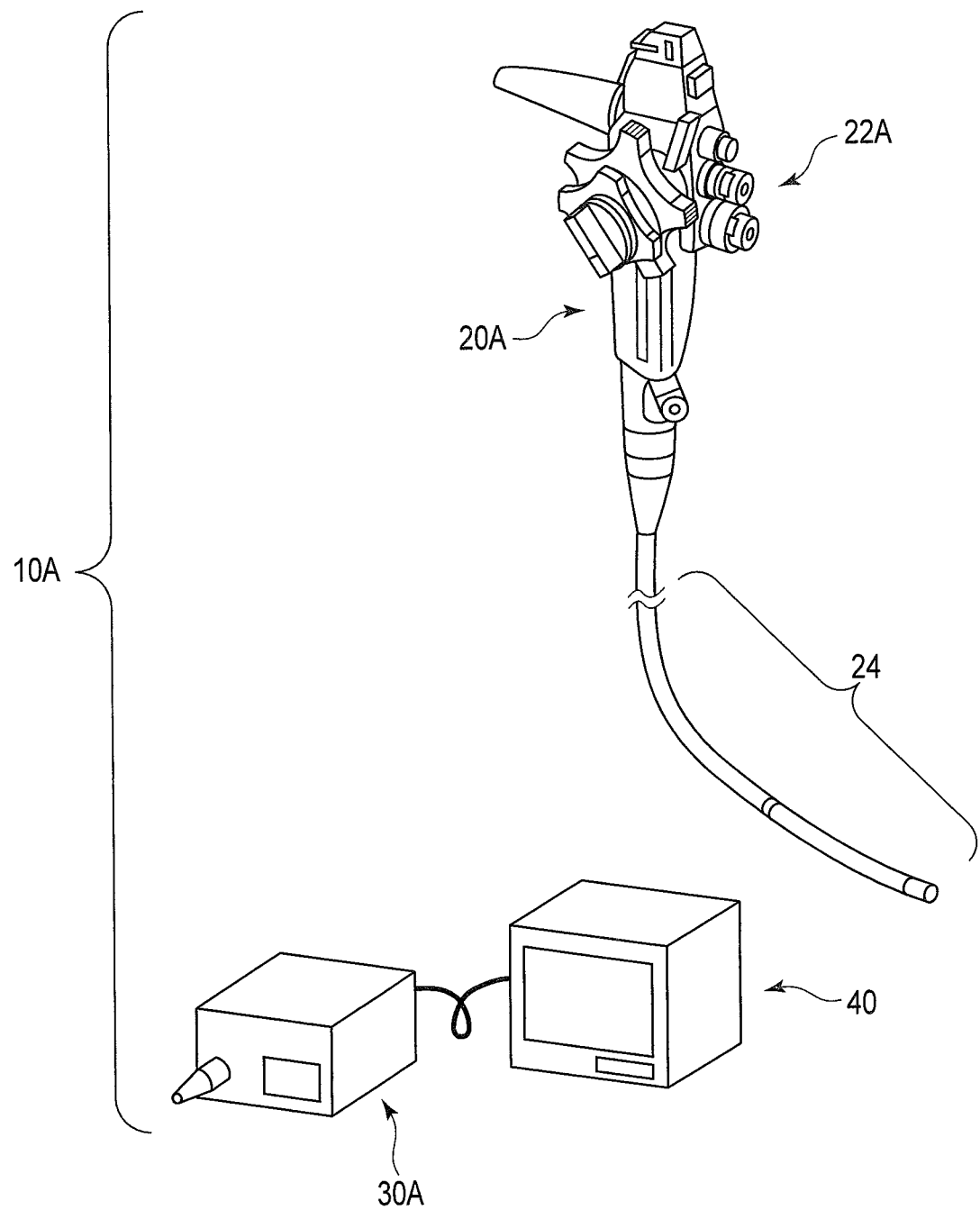
FIG. 3 shows another endoscope system according to the first embodiment.

FIG. 3 shows another endoscope system 10A according to the present embodiment. In the endoscope system 10 shown in FIG. 1, the endoscope 20 and the control device 30 are connected to each other by the universal cord 26, but in the endoscope system 10A shown in FIG. 3, the universal cord is not present and an endoscope 20A is a wireless endoscope, such that a signal transmission between the endoscope 20A and a control device 30A is wirelessly performed. Further, the present invention is not limited to the configuration of the wireless endoscope, and an image may be transmitted in a wired manner and the light source may be placed on the control section of the endoscope.

Figure 4:
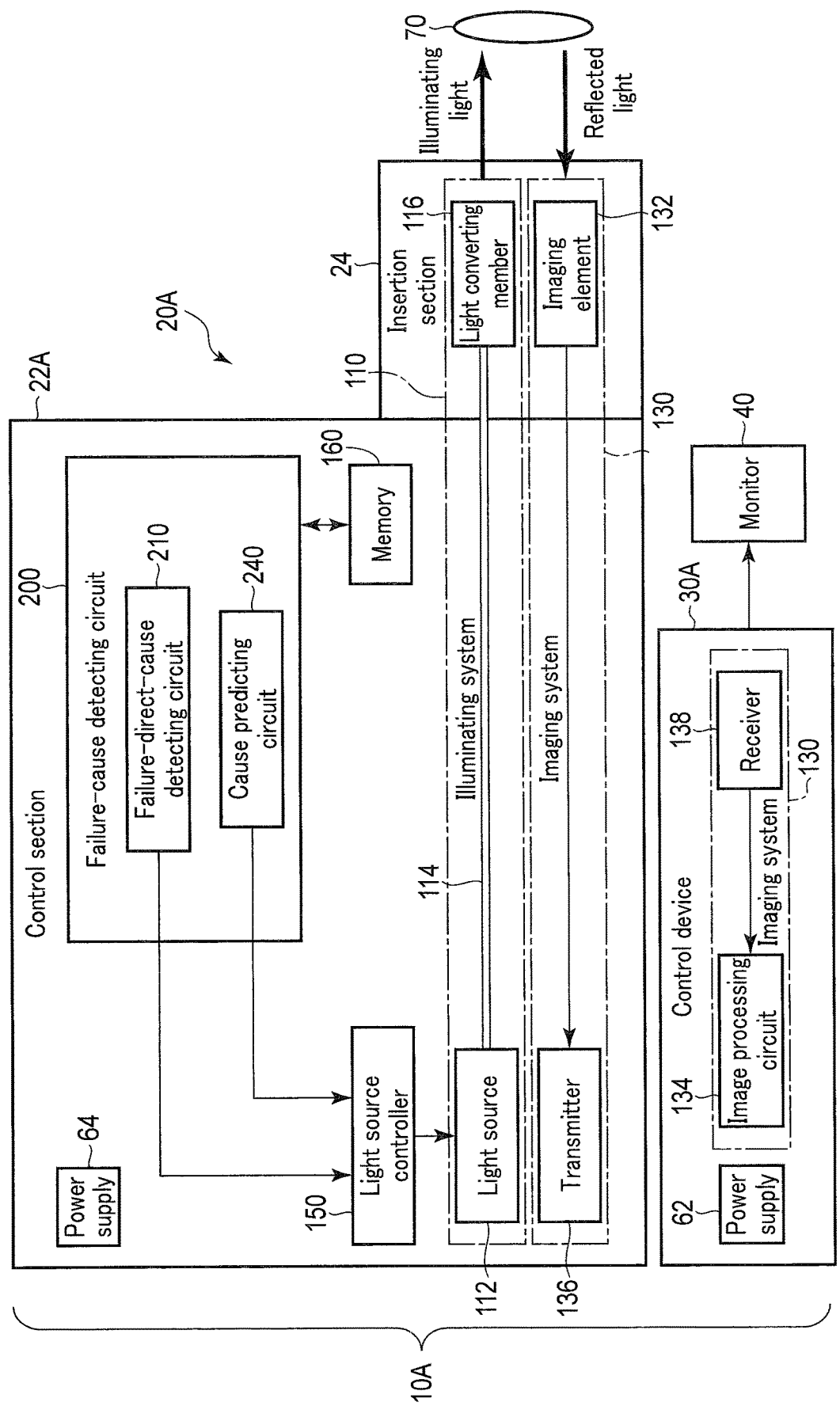
FIG. 4 shows function blocks of the endoscope system shown in FIG. 3.

Since the wireless endoscope is applied, the configuration of the endoscope 20A and the control device 30A is different from that of the endoscope 20 and the control device 30 of FIG. 1. FIG. 4 shows function blocks of the endoscope system 10A shown in FIG. 3. As shown in FIG. 4, the light source 112 and the light source controller 150, which are disposed in the control device 30 in the endoscope system 10 shown in FIG. 1, are disposed in a control section 22A. In addition, a power supply 64 for driving the endoscope 20A is provided inside the control section 22A.

The imaging system 130 includes a transmitter 136 configured to wirelessly transmit an image signal from the imaging element 132 and a receiver 138 configured to receive the image signal transmitted from the transmitter 136. The transmitter 136 is disposed in the control section 22A. The receiver 138 is disposed in the control device 30A. In addition, the power supply 62 for driving the control device 30A is provided in the control device 30A.

Since the wireless endoscope system 10A can have a free layout without being limited to the universal cord when the endoscope 20A is used, or can change an attitude/position of the endoscope 20 without being pulled out by the universal cord, because the universal cord is not present, that is, the wireless endoscope system 10A has excellent convenience.

Hereinafter, the endoscope system 10 shown in FIG. 1 is typically described, but the contents thereof may be applied to the wireless endoscope system 10A shown in FIG. 3.

Hereinafter, each configuration of the endoscope system 10 will be described in detail.

<Illuminating System 110>

Primary light output from the light source 112 is guided by the optical fibers 118 and 114, is converted into illuminating light of desired optical characteristics by the light converting member 116, and is output to the outside. The light converting member 116 may include, for example, a wavelength converting member. The wavelength converting member may include, for example, a fluorescent substance configured to absorb the primary light and generate fluorescent light (illuminating light) having a wavelength different from that of the primary light. Alternatively, the light converting member 116 may include a diffusing member configured to diffuse the primary light without converting the wavelength of the primary light. The diffusing member has a diffusion angle wider than that of the primary light and generates diffuse light (illuminating light) having low coherence. The light converting member may include both the wavelength converting member and the diffusing member.

<Light Source 112>

The light source 112 includes a laser diode configured to output the primary light, for example, blue laser light, having high coherence such as laser light, for example. A center wavelength of the blue laser light is, for example, 445 nm. The center wavelength of the laser light need not be limited thereto. The light source 112 includes a lens (not shown) disposed in front of the laser diode. The light source 112 includes a receptacle (not shown) to which the optical fiber 118 is connected. The light source 112 may have a pigtail instead of having the receptacle.

<Optical Connector 120>

The optical connector 120 is a portion configured to optically connect the optical fiber 118 connected to the light source 112 and the optical fiber 114 to each other, for example, when the endoscope 20 is connected to the control device 30 through the universal cord 26. Alternatively, the optical connector 120 is a portion configured to optically connect the pigtail of the light source 112 and the optical fiber 114 to each other. A member called a ferrule is fixed to a tip end of the optical fiber 114, and the tip end of the optical fiber 114 is optically connected and fixed to a tip end of the optical fiber 118 on the other side by pressing the ferrule.

The light source 112 and the optical fiber 114 may be directly connected to each other.

<Optical Fiber 114>

The optical fiber 114 has a function of guiding the blue laser light output from the control device 30 to the distal end of the insertion section 24. The optical fiber 114 according to the present embodiment is, for example, a multimode optical fiber with a core diameter of 50 μm and numerical aperture NA of 0.2. Multimode optical fibers with different core diameters and numerical apertures may be used. The optical fiber 114 is formed of, for example, glass or plastic. Most of the optical fiber 114 is covered by, for example, a cover layer (not shown) formed of a resin material that protects the optical fiber 114.

<Light Converting Member 116>

The light converting member 116 is a member configured to change optical characteristics of the primary light from the light source 112. The light converting member 116 includes, for example, a wavelength converting member. The wavelength converting member includes, for example, a fluorescent substance configured to absorb the primary light from the light source 112 and generate light having a wavelength different from that of the primary light, that is, perform a wavelength conversion. The fluorescent substance is a powder represented by, for example, YAG:Ce. The fluorescent substance has a function of absorbing the primary light of a blue wavelength range and performing a wavelength conversion for the primary light to yellow fluorescent light, which is the illuminating light. In addition, since the fluorescent light is emitted without directivity, the fluorescent substance also has a diffusion function. The powdered fluorescent substance is contained in a sealing member in a dispersed state.

Hereinafter, the light converting member 116 is described as being the fluorescent substance.

<Failure-Cause Detecting Circuit 200>

The failure-cause detecting circuit 200 includes a failure-direct-cause detecting circuit 210 configured to detect a first pre-failure state that has a possibility of directly causing the failure of a component of the endoscope 20 and a cause predicting circuit 240 configured to detect a second pre-failure state in which it is predicted that the endoscope 20 reaches the first pre-failure state from a typically operating state as a failure prediction.

<Light Source Controller 150>

The light source controller 150 reduces quantity of light of the light source 112 or stops the light source 112 based on the detection result of the failure-cause detecting circuit 200.

<Failure-Direct-Cause Detecting Circuit 210>

Figure 5:
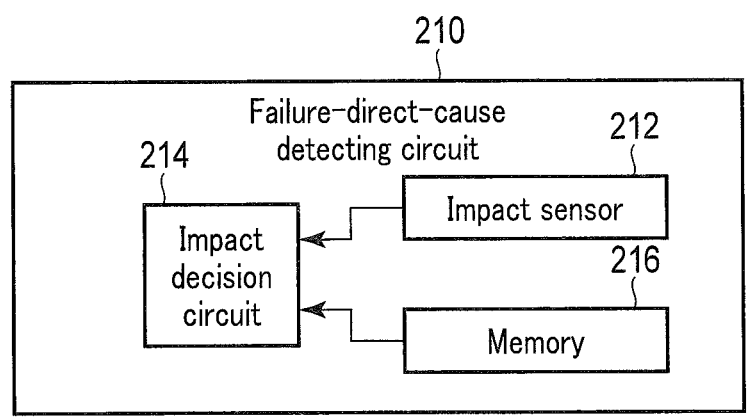
FIG. 5 shows a configuration example of a failure-direct-cause detecting circuit shown in FIG. 2.

FIG. 5 shows a configuration example of a failure-direct-cause detecting circuit 210 shown in FIG. 2. As shown in FIG. 5, the failure-direct-cause detecting circuit 210 includes an impact sensor 212 configured to detect impact applied to the endoscope 20, an impact decision circuit 214 configured to decide the impact detected by the impact sensor 212, and a memory 216 storing a threshold value of the impact decision. The impact sensor 212 is provided in the control section 22 or in the distal end of the insertion section 24.

The impact sensor 212 detects impact applied to the control section 22 or the insertion section 24 and outputs a signal corresponding to the impact to the impact decision circuit 214. The impact decision circuit 214 compares the output signal of the impact sensor 212 with the threshold value stored in the memory 216. When the output signal of the impact sensor 212 exceeds the threshold value, the impact decision circuit 214 decides that the endoscope 20 is in the first pre-failure state, which is a phenomenon of directly causing the failure of a component of the endoscope 20. The first pre-failure state is, for example, a state in which the endoscope 20 comes in contact with or collides with a wall or a floor, thereby causing the impact. The failure-direct-cause detecting circuit 210 outputs the decision result, that is, information on the detection of the first pre-failure state to the light source controller 150.

In a case in which the information on the detection of the first pre-failure state is input to the light source controller 150, the light source controller 150 reduces the quantity of light of the light source 112 to quantity of light at a level with less influence on the human body. For example, the light source controller 150 reduces the quantity of light of the light source 112 to the quantity of light set to the class 2 or less of a safety reference of laser. In a case of non-visible light, the quantity of light may be reduced to the quantity of light set to the class 1 or less. In addition, even in the case of visible light, in order to obtain quantity of output light of a lower level, the quantity of light may be reduced to the class 1 or less.

In addition, a constitution in which the quantity of output light of the light source is reduced to a predetermined set quantity of light is shown, but the set quantity of light may be defined based on a failure occurrence possibility and quantity of light that leaks when a failure occurs at the portion on a path from the light source to an output aperture of the illuminating light.

In addition, the failure-direct-cause detecting circuit 210 outputs the information on the detection of the first pre-failure state to the memory 160. The memory 160 stores the information on the detection of the first pre-failure state as a history such as a collision of the endoscope 20 with a wall, a floor, or the like. A threshold value of the detection of the first pre-failure state may be changed based on the history stored in the memory 160.

The impact sensor 212 is preferably disposed at a position that is downward in a normal use direction of the endoscope 20, a position close to the center of gravity, or a position with which the control section 22 first comes in contact when the control section 22 falls. This facilitates detection of the first pre-failure state earlier. Alternatively, the impact sensor 212 may be disposed at a position at which it is easy to come in contact with an external substance outside the control section 22. The impact sensor 212 may be disposed at a position at which leakage of laser light is concerned when the illuminating system is damaged in the control section 22 or the insertion section 24, for example, on the periphery of the optical fiber 114, on the periphery of the light converting member 116, or on the periphery of an optical coupler 302, or, in the case of a wireless type, on the periphery of the light source 112.

<Cause Predicting Circuit 240>

Figure 6:
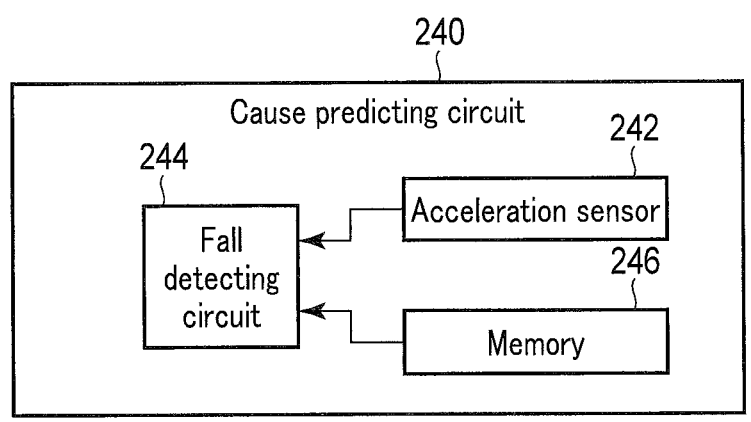
FIG. 6 shows a configuration example of a cause predicting circuit shown in FIG. 2.

FIG. 6 shows a configuration example of a cause predicting circuit 240 shown in FIG. 2. As shown in FIG. 6, the cause predicting circuit 240 includes an acceleration sensor 242 configured to detect acceleration applied to the endoscope 20, a fall detecting circuit 244 configured to detect a fall of the endoscope 20 based on the acceleration detected by the acceleration sensor 242, and a memory 246 storing a threshold value of a decision of the fall detection.

The acceleration sensor 242 is provided in the control section 22 or in the distal end of the insertion section 24. The acceleration sensor 242 may be provided at a position at which leakage of laser light is concerned when the illuminating system is damaged in the control section 22 or the insertion section 24, for example, on the periphery of the optical fiber 114, on the periphery of the light converting member 116, or on the periphery of the optical coupler 302, or, in the case of a wireless type, on the periphery of the light source 112.

The acceleration sensor 242 detects acceleration applied to the control section 22 or the insertion section 24, for example, acceleration of gravity, and outputs a signal corresponding to the acceleration to the fall detecting circuit 244. The fall detecting circuit 244 compares the output signal of the acceleration sensor 242 with the threshold value stored in the memory 246. In a case in which the output signal of the acceleration sensor 242 falls below the threshold value, the fall detecting circuit 244 decides that the endoscope 20 is in the second pre-failure state before reaching the first pre-failure state. The second pre-failure state is a state in which the endoscope is likely to reach to the first pre-failure state. For example, the second pre-failure state is a state in which the endoscope 20 is falling. When the control section 22 is held in the hand, the acceleration (acceleration of gravity, approximately 9.8 m/s$^2$) is detected by the acceleration sensor 242, but when the control section 22 is separated from the hand and falls, the acceleration is reduced. The threshold value of the fall detection may be, for example, a value that is reduced by about 50% or more with respect to an initial value. In order to detect the fall more reliably, the threshold value may be a value that is reduced by 20% or more with respect to the initial value. In addition, in order to prevent a false detection, the threshold value may be a value that is reduced by 80% or more with respect to the initial value. The cause predicting circuit 240 outputs the decision result, that is, information on the detection of the second pre-failure state to the light source controller 150.

In a case in which the information on the detection of the second pre-failure state, that is, the detection of the fall is input to the light source controller 150, the light source controller 150 reduces quantity of light of the light source 112 to quantity of light at a level with less influence on the human body. For example, the light source controller 150 reduces the quantity of light of the light source 112 to the quantity of light set to the class 2 or less of a safety reference of laser.

The acceleration sensor 242 can detect any falling direction by taking the square root of the sum of squares and determining the fall using the value, using the detection of the acceleration in three axes.

(Action)

Figure 7:
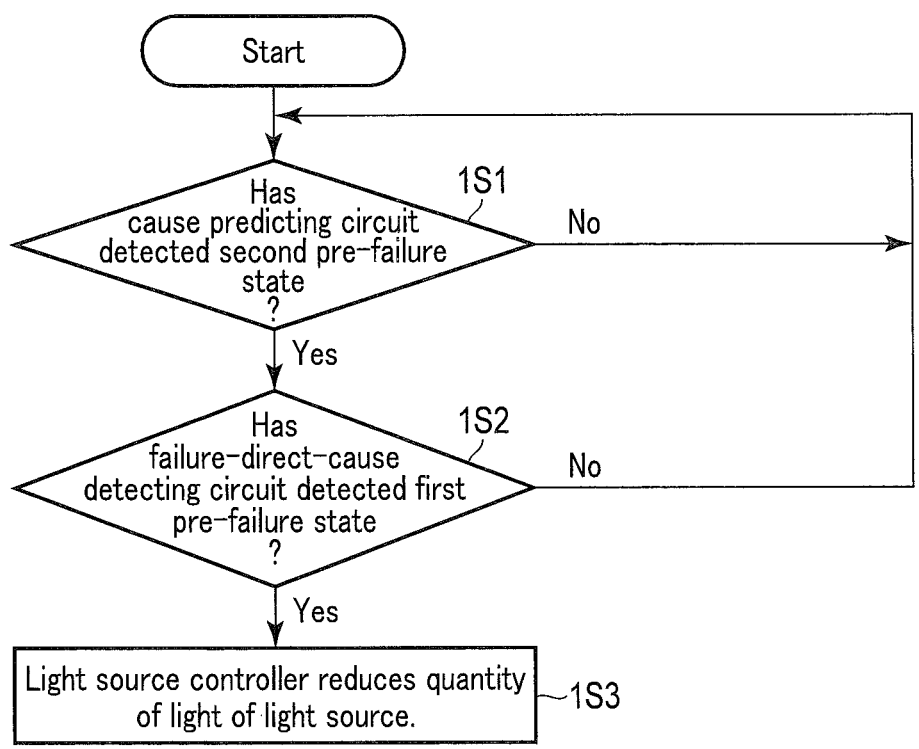
FIG. 7 shows an overall flow of a corresponding process of a case in which the endoscope of the endoscope system according to the first embodiment falls down and then collides with a floor.

FIG. 7 shows an overall flow of a corresponding process of a case in which the endoscope 20 of the endoscope system 10 according to the present embodiment falls down and then collides with a floor.

In a first step (1S1), the cause predicting circuit 240 decides whether or not the endoscope 20 is in the second pre-failure state. In a case in which the endoscope 20 is separated from the hand and falls, the cause predicting circuit 240 detects a free fall of the endoscope 20 based on the output of the acceleration sensor 242 and decides that the endoscope 20 is in the second pre-failure state. In a case in which it is detected that a free fall state is continued for a predetermined period, the cause predicting circuit 240 may decide that the endoscope 20 is in the second pre-failure state. The predetermined period may be a value corresponding to a time period necessary for falling corresponding to a height at which a possibility of failure due to the falling becomes high.

In a case in which the cause predicting circuit 240 does not detect the free fall of the endoscope 20 and decides that the endoscope 20 is not in the second pre-failure state, the light source controller 150 does not particularly change an operation of the light source 112 and the endoscope system 10 is maintained in a state in which the endoscope system 10 can continue to be used as it is.

In a case in which the cause predicting circuit 240 detects the free fall of the endoscope 20 and decides that the endoscope 20 is in the second pre-failure state, in a next step (1S2), the failure-direct-cause detecting circuit 210 decides whether or not the endoscope 20 is in the first pre-failure state. In a case in which the endoscope 20 is falling, the endoscope 20 is in a state in which it falls down and then collides with a floor.

In a case in which the failure-direct-cause detecting circuit 210 decides that the endoscope 20 is not in the first pre-failure state, the light source controller 150 does not particularly change an operation of the light source 112 and the endoscope system 10 is maintained in a state in which the endoscope system 10 can continue to be used as it is.

In a case in which the failure-direct-cause detecting circuit 210 decides that the endoscope 20 is in the first pre-failure state, in a next step (1S3), the light source controller 150 reduces the quantity of light of the light source 112.

The detection of the first pre-failure state is performed in a case of detecting that the endoscope 20 is in the second pre-failure state, the detection of the first pre-failure state and the detection of the second pre-failure state may be performed simultaneously or sequentially.

The quantity of light of the light source 112 is reduced after detecting the first pre-failure state, but the quantity of light of the light source 112 may be reduced after detecting the second pre-failure state. In this case, when it is decided that the endoscope 20 is not in the first pre-failure state in a subsequent detection of the first pre-failure state, the light source controller 150 preferably releases a reduction state of the quantity of light of the light source 112 to return the endoscope system 10 to a normal use state.

Alternatively, after it is decided that the endoscope is not in the first pre-failure state and a predetermined time is then elapsed, the light source controller 150 may release the reduction state of the quantity of light of the light source 112 to return the endoscope system 10 to the normal use state. Alternatively, after the second pre-failure state is detected and a predetermined time is then elapsed, the detection of the first pre-failure state may be performed.

Here, an operation example in which the light source controller 150 reduces the quantity of light of the light source 112 depending on the detection of the first pre-failure state is described, but the light source controller 150 may stop the light source 112 depending on the detection of the first pre-failure state.

(Effect)

Since the light source controller 150 reduces the quantity of light of the light source 112 based on information of the failure-direct-cause detecting circuit 210, it is possible to obtain an effect in which laser light can be prevented from leaking at an unexpectedly high level.

Since the cause predicting circuit 240 detects the fall of the endoscope 20 and the failure-direct-cause detecting circuit 210 then detects impact applied to the endoscope 20 to detect the pre-failure state in two steps of the fall detection and the impact detection, it is possible to obtain an effect in which an operation of an ordinary control of the endoscope 20 can be reduced from being erroneously detected as a state of falling or the like.

It is possible to obtain an effect in which laser safety can be secured before a component of the endoscope 20 fails by changing, by the failure-direct-cause detecting circuit 210, the threshold value of the detection of the first pre-failure state based on magnitude of the impact detected by the impact sensor 212.

First Modified Example of First Embodiment (Configuration)

The present modified example aims at another configuration example of the cause predicting circuit 240.

<Cause Predicting Circuit 240>

Figure 8:
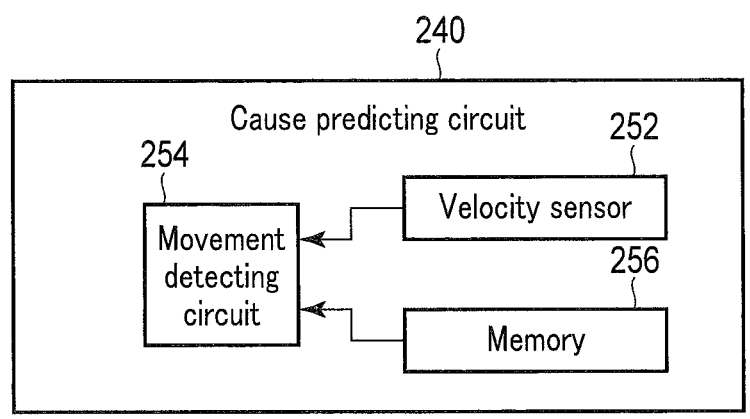
FIG. 8 shows a configuration example of a cause predicting circuit according to a first modified example of the first embodiment.

FIG. 8 shows a configuration example of a cause predicting circuit 240 according to the present modified example. As shown in FIG. 8, the cause predicting circuit 240 includes a velocity sensor 252 configured to detect velocity of the endoscope 20, a movement detecting circuit 254 configured to detect a movement of the endoscope 20 based on the velocity detected by the velocity sensor 252, and a memory 256 storing a threshold value of a decision of the movement detection.

The velocity sensor 252 is provided in the control section 22 or in the distal end of the insertion section 24. The velocity sensor 252 may be provided at a position at which leakage of laser light is concerned when the illuminating system is damaged in the control section 22 or the insertion section 24, for example, on the periphery of the optical fiber 114, on the periphery of the light converting member 116, or on the periphery of the optical coupler 302, or, in the case of a wireless type, on the periphery of the light source 112.

The velocity sensor 252 detects velocity applied to the control section 22 or the insertion section 24, and outputs a signal corresponding to the velocity to the movement detecting circuit 254. The movement detecting circuit 254 compares the output signal of the velocity sensor 252 with the threshold value stored in the memory 256. In a case in which the output signal of the velocity sensor 252 exceeds the threshold value, or in a case in which the output signal of the velocity sensor 252 continues to exceed the threshold value for a period of time longer than a predetermined time (e.g., longer than 1 second), the movement detecting circuit 254 decides that the endoscope 20 is in the second pre-failure state before reaching the first pre-failure state. The second pre-failure state is, for example, a state in which the control section 22 is abruptly and vigorously separated from the hand (corresponding to a state in which the control section 22 is thrown). The cause predicting circuit 240 outputs information on the detection of the second pre-failure state to the light source controller 150.

A method for setting velocity corresponding to a height of a falling start to the threshold value is described below. When the endoscope 20 is free-falling, the velocity is increased by acceleration of gravity. By assuming that the endoscope falls from a height at which it is predicted that the endoscope is broken, the velocity reached by the acceleration of gravity when the endoscope falls from the height may be set to the threshold value. By detecting that the velocity is exceeded, it is possible to detect a fall from a predetermined height, that is, a height at which a failure is expected. For example, if an occurrence frequency of the failure is increased when the endoscope falls from the height of 1 m, when a height from a floor is y, acceleration of gravity g is 9.8 m/s$^2$, and velocity when the endoscope reaches the floor is v, since a relationship of v$^2$=2 gy is established among y, g, and v, approximately 4.4 m/s may be set to the threshold value. When velocity equal to or higher than the velocity is detected, it is decided that the endoscope falls from the height of 1 m or more and it is decided that the endoscope is in the second pre-failure state. The threshold value may be corrected in consideration of air resistance at the time of falling. In this case, the threshold value may be determined in consideration of air resistance by a shape of the endoscope.

In addition, in a case in which the control section 22 is vigorously separated from the hand, or in a case in which even if the control section 22 is held by the hand, the endoscope 20 is moved at velocity predicted to cause the above-mentioned failure, velocity corresponding to the case may be set to the threshold value.

In a case in which the information on the detection of the second pre-failure state is input from the cause predicting circuit 240, the light source controller 150 reduces quantity of light of the light source 112 to quantity of light at a level with less influence on the human body. For example, the light source controller 150 reduces the quantity of light of the light source 112 to the quantity of light set to the class 2 or less of a safety reference of laser.

(Effect)

Since the light source controller 150 reduces the quantity of light of the light source 112 based on information of the cause predicting circuit 240, for example, based on information of the movement at the velocity at which the failure is expected, it is possible to obtain an effect in which laser light can be prevented from leaking at an unexpectedly high level.

Second Modified Example of First Embodiment (Configuration)

The present modified example aims at another configuration example of the cause predicting circuit 240.

<Cause Predicting Circuit 240>

Figure 9:
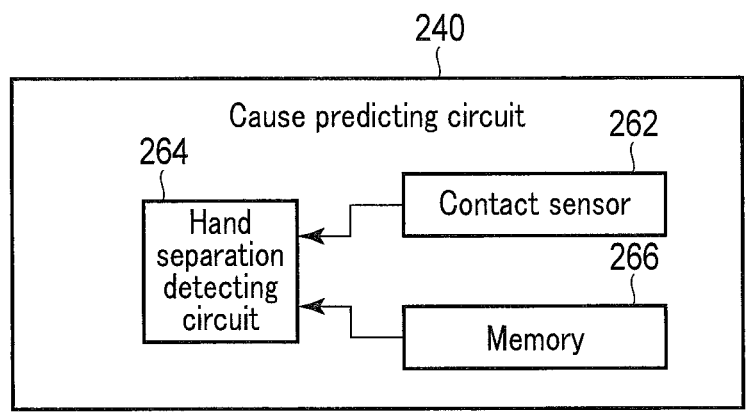
FIG. 9 shows a configuration example of a cause predicting circuit according to a second modified example of the first embodiment.

FIG. 9 shows a configuration example of a cause predicting circuit 240 according to the present modified example. As shown in FIG. 9, the cause predicting circuit 240 includes a contact sensor 262 configured to detect that the control section 22 of the endoscope 20 is held by the hand, a hand separation detecting circuit 264 configured to detect that the control section 22 is separated from the hand based on an output of the contact sensor 262, and a memory 266 storing a threshold value of a decision of the hand separation detection.

The contact sensor 262 is provided to a portion of the control section 22 that is in contact with an operator's hand when the operator of the endoscope 20 normally holds the control section 22. The contact sensor 262 may be constituted of a simple switch. When the control section 22 is in contact with the operator's hand, the switch of the contact sensor 262 is pushed by a finger or the like, and the contact sensor is turned on and outputs contact information. In addition, when the control section 22 is separated from the operator's hand, the switch of the contact sensor 262 is turned off and the contact sensor 262 outputs non-contact information. As the contact sensor, for example, a capacitive contact sensor may be used.

In a case in which the non-contact information is input from the contact sensor 262, the hand separation detecting circuit 264 compares duration of the input of the non-contact information with the threshold value stored in the memory 266. In a case in which the duration of the input of the non-contact information exceeds the threshold value (e.g., 0.5 seconds), the hand separation detecting circuit 264 decides that the endoscope 20 is in the second pre-failure state before reaching the first pre-failure state. The second pre-failure state is, for example, a state in which the control section 22 is separated from the operator's hand and is falling.

In a case in which the information on the detection of the second pre-failure state is input from the cause predicting circuit 240, the light source controller 150 reduces quantity of light of the light source 112 to quantity of light at a level with less influence on the human body. For example, the light source controller 150 reduces the quantity of light of the light source 112 to the quantity of light set to the class 2 or less of a safety reference of laser.

Second Embodiment (Configuration)

Figure 10:
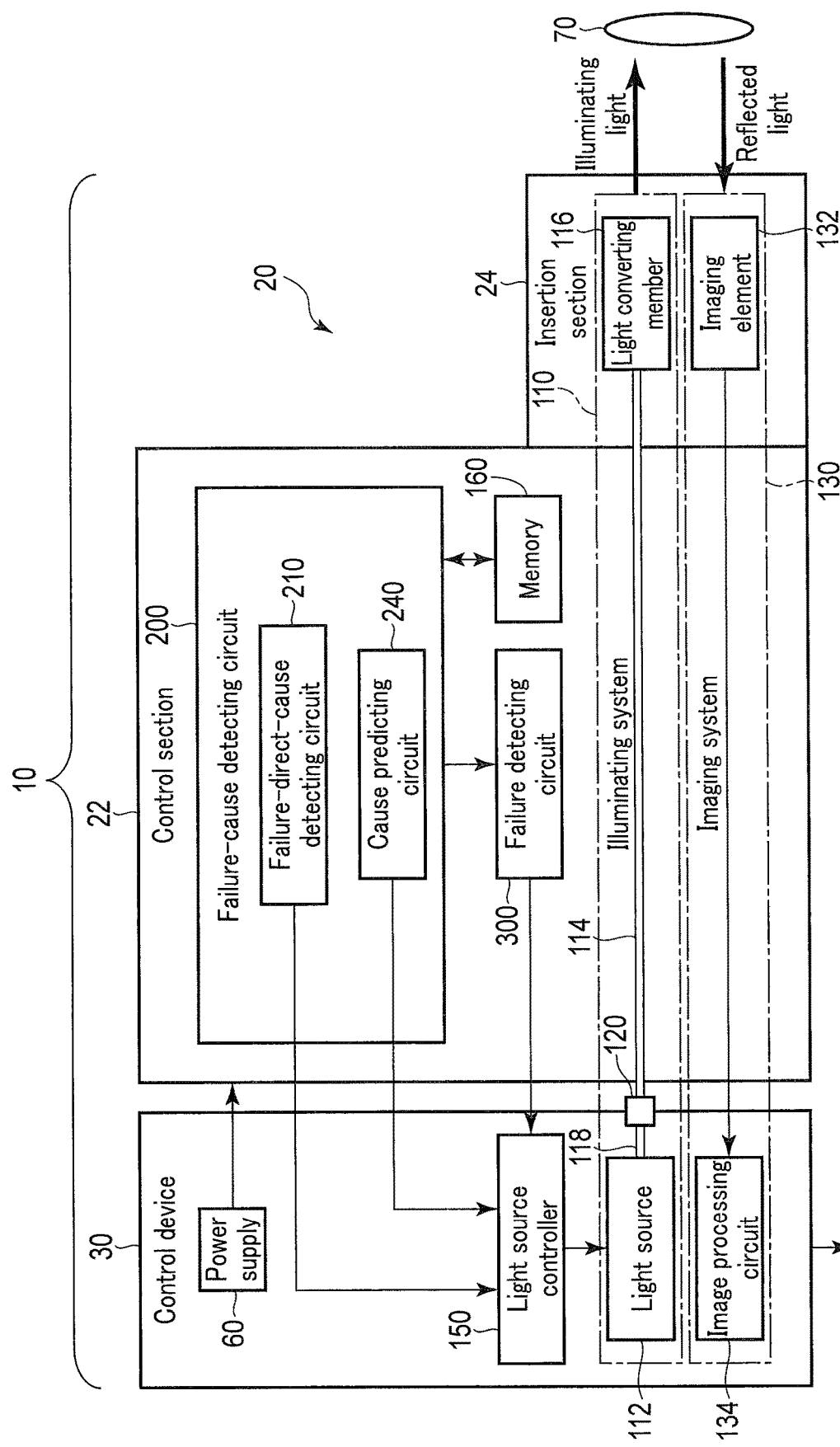
FIG. 10 shows function blocks of an endoscope system according to a second embodiment.

FIG. 10 shows function blocks of the endoscope system 10 according to the present embodiment. In FIG. 10, the members indicated by the same reference numerals as those shown in FIG. 2 are the same members, and a detailed description thereof will be omitted. Hereinafter, different portions are mainly described. That is, portions that are not mentioned in the following description are the same as those of the first embodiment.

In the endoscope system 10, the endoscope 20 includes a failure detecting circuit 300 in addition to the failure-cause detecting circuit 200 as shown in FIG. 10. In other words, the endoscope 20 according to the present embodiment has a configuration in which the failure detecting circuit 300 is added to the endoscope 20 according to the first embodiment.

<Failure Detecting Circuit 300>

The failure detecting circuit 300 decides whether or not a failure occurs in each member constituting the illuminating system 110 and outputs the decision result to the light source controller 150. The failure detecting circuit 300 starts depending on the detection of the pre-failure state by the failure-cause detecting circuit 200.

<Light Source Controller 150>

The light source controller 150 reduces quantity of light of the light source 112 or stops the light source 112 based on the detection results of the failure-cause detecting circuit 200 and the failure detecting circuit 300.

<Failure Detecting Circuit 300>

FIG. 11 shows a configuration example of the failure detecting circuit 300 shown in FIG. 10. As shown in FIG. 11, the failure detecting circuit 300 includes an optical coupler 302 provided in the optical fiber 114, an optical fiber 304 connected to the optical coupler 302, a light detector 306 optically connected to the optical fiber 304, a light quantity decision circuit 308 configured to decide the quantity of light detected by the light detector 306, and a memory 310 storing a threshold value of the decision of the quantity of light.

The optical coupler 302 is a two-input and two-output optical coupler and has two input terminals and two output terminals. One input terminal is connected to the light source 112 and is input with laser light. The other input terminal is connected to the light detector 306 through the optical fiber 304. The two output terminals are connected to the light converting members 116, respectively. The optical coupler 302 branches and outputs the light input to one input terminal into the two output terminals. Therefore, the illuminating system 110 shown in FIG. 11 includes two light converting members 116. A light quantity ratio (a branch ratio) at which the optical coupler 302 branches the light is 50:50, and the illuminating system 110 is constituted of two lamps.

The failure detecting circuit 300 may have an optical filter that transmits light of a specific wavelength between the optical coupler 302 and the light detector 306. The optical filter may have characteristics that it does not transmit light of a wavelength equal to the light output from the light source 112 and transmits light of a wavelength of fluorescent light generated in the light converting member 116 (fluorescent substance). Thereby, return light of fluorescent light generated in the light converting member 116 is selectively detected by the light detector 306.

The light from the light source 112 is guided by the optical fiber 114, enters one input terminal of the optical coupler 302, is branched by the optical coupler 302, and is output to the two output terminals. The light output from the two output terminals of the optical coupler 302 is guided by the optical fibers 114 and enters the light converting members 116. The light converting members 116 (fluorescent substances) absorb part of the incoming light and generate fluorescent light. Part of the fluorescent light generated by the light converting members 116 is guided by the optical fibers 114, enters the output terminals of the optical coupler 302, is branched by the optical coupler 302, and is output from the two input terminals. The light output from the input terminal to which the optical fiber 304 is connected is guided by the optical fiber 304 and enters the light detector 306. The light detector 306 outputs an electrical signal according to quantity of incoming light to the light quantity decision circuit 308.

In a case in which an optical fiber 114 is folded or damaged by the fall of the endoscope 20 or an impact at the time of falling, or in a case in which a light converting member 116 (fluorescent substance) is inclined with respect to the corresponding optical fiber 114 or is separated from the corresponding optical fiber 114, the return light from the light converting members 116 at the distal end of the insertion section 24 is reduced. The light quantity decision circuit 308 compares the output signal of the light detector 306 with the threshold value stored in the memory 310. The threshold value is set to a value of quantity of the return light that does not fall below in a state in which the failure does not occur in a state in which the quantity of light of the light source 112 is reduced. For example, the threshold value may be, but not limited to, 80% of the quantity of light of the return light in the state in which the failure does not occur in the state in which the quantity of light of the light source 112 is reduced. In a case in which the output signal of the light detector 306 falls below the threshold value, the light quantity decision circuit 308 decides that an optical fiber 114 or a light converting member 116 (fluorescent substance) fails. The failure detecting circuit 300 outputs the decision result to the light source controller 150. Since the quantity of return light depends on the quantity of light entering the light converting members from the light source, the threshold value may be increased or decreased in accordance with the increase or decrease of the quantity of light of the light source.

In a case in which the failure is not detected, the light source controller 150 returns the quantity of light of the light source 112 to normal quantity of light. On the contrary, in a case in which the failure is detected, the light source controller 150 stops the light source 112. In addition, the control device 30 warns that the illuminating system 110 has a failure and needs repair through the monitor 40.

The failure may be confirmed by passing light for failure detection through the optical fibers 114 separately from the light exciting the light converting members 116 (fluorescent substances) to detect the return light.

A power supply for driving the failure-direct-cause detecting circuit 210 and the cause predicting circuit 240 may be embedded in the endoscope 20, such that the failure-direct-cause detecting circuit 210 and the cause predicting circuit 240 are always driven even in a state in which the endoscope system 10 is not used. Thereby, for example, in a case in which the endoscope 20 collides with an obstacle in a state in which a supply of power from the control device 30 is stopped such as when the endoscope 20 is cleaned, such a fact is recorded in the memory 160. Thereafter, in a case in which a record of a history such as a collision or the like is recorded when the endoscope system 10 is operated, for example, the failure detecting circuit 300 starts a failure detection operation. Alternatively, a message warning that abnormality occurs during the stop of the endoscope system 10 may be displayed on the monitor 40. Additionally, in addition to the failure-direct-cause detecting circuit 210 and the cause predicting circuit 240, the failure detecting circuit 300 may also always be driven.

(Action)

FIG. 12 shows an overall flow of a corresponding process of a case in which the endoscope 20 of the endoscope system 10 according to the present embodiment falls down and then collides with a floor.

In a first step (2S1), the cause predicting circuit 240 decides whether or not the endoscope system 10 is in the second pre-failure state. In a case in which the endoscope 20 is separated from the hand and falls, the cause predicting circuit 240 detects a free fall of the endoscope 20 based on the output of the acceleration sensor 242 and decides that the endoscope 20 is in the second pre-failure state. In a case in which it is detected that a free fall state is continued for a predetermined period, the cause predicting circuit 240 may decide that the endoscope 20 is in the second pre-failure state. The predetermined period may be a value corresponding to a time period necessary for falling corresponding to a height at which a possibility of failure due to the falling becomes high.

In a case in which the cause predicting circuit 240 does not detect the free fall of the endoscope 20 and decides that the endoscope 20 is not in the second pre-failure state, the light source controller 150 does not particularly change an operation of the light source 112 and the endoscope system 10 is maintained in a state in which the endoscope system 10 can continue to be used as it is.

In a case in which the cause predicting circuit 240 detects the free fall of the endoscope 20 and decides that the endoscope 20 is in the second pre-failure state, in a next step (2S2), the failure-direct-cause detecting circuit 210 decides whether or not the endoscope 20 is in the first pre-failure state. In a case in which the endoscope 20 is falling, the endoscope 20 is in a state in which it falls down and then collides with a floor.

In a case in which the failure-direct-cause detecting circuit 210 decides that the endoscope 20 is not in the first pre-failure state, the light source controller 150 does not particularly change an operation of the light source 112 and the endoscope system 10 is maintained in a state in which the endoscope system 10 can continue to be used as it is.

In a case in which the failure-direct-cause detecting circuit 210 decides that the endoscope 20 is in the first pre-failure state, in a next step (2S3), the light source controller 150 reduces the quantity of light of the light source 112.

Subsequently, in a next step (2S4), the failure detecting circuit 300 starts to decide whether or not the failure occurs in the illuminating system 110.

In a case in which the failure detecting circuit 300 decides that the failure occurs in the illuminating system 110, in a step (2S5), the light source controller 150 stops the light source 112. Additionally, the control device 30 may display a message prompting a user to perform the repair on the monitor 40. In addition, the control device 30 may prompt the user to perform the repair by issuing a warning sound.

In a case in which the failure detecting circuit 300 decides that the failure does not occur in the illuminating system 110, in a step (2S6), the light source controller 150 releases a limitation of the quantity of light of the light source 112 to return the light source 112. In addition, the memory 160 stores that the endoscope 20 reaches the first pre-failure state.

Since a detection history of the first pre-failure state, that is, the extent to which the endoscope 20 has been impacted is stored in the memory 160, the user (a doctor or the like) or maintenance personnel can access information stored in the memory 160 before repair or maintenance to confirm the damage to the endoscope 20.

In addition, based on the information stored in the memory 160, the threshold value of the decision of the first pre-failure state or the threshold value of the decision of the failure detecting circuit 300 may be changed. For example, in a case in which the number of detection of the first pre-failure state increases, since it is expected that the damage to the illuminating system 110 is accumulated, it may be decided that the endoscope is in the first pre-failure state even with a smaller impact by setting the threshold value of the decision of the first pre-failure state to be small. It is also good to have information on each strength.

A detection history of the second pre-failure state may be similarly stored in the memory 160.

The detection of the first pre-failure state is performed in a case of detecting that the endoscope 20 is in the second pre-failure state, the detection of the first pre-failure state and the detection of the second pre-failure state may be performed simultaneously or sequentially.

The quantity of light of the light source 112 is reduced after detecting the first pre-failure state, but the quantity of light of the light source 112 may be reduced after detecting the second pre-failure state. In this case, when it is decided that the endoscope 20 is not in the first pre-failure state in a subsequent detection of the first pre-failure state, the light source controller 150 preferably releases a reduction state of the quantity of light of the light source 112 to return the endoscope system 10 to a normal use state.

Alternatively, after it is decided that the endoscope is not in the first pre-failure state and a predetermined time is then elapsed, the light source controller 150 may release the reduction state of the quantity of light of the light source 112 to return the endoscope system 10 to the normal use state. Alternatively, after the second pre-failure state is detected and a predetermined time is then elapsed, the detection of the first pre-failure state may be performed.

(Effect)

Since the light source controller 150 reduces the quantity of light of the light source 112 based on information of the failure-direct-cause detecting circuit 210, it is possible to obtain an effect in which laser light can be prevented from leaking at an unexpectedly high level.

Since the cause predicting circuit 240 detects the fall of the endoscope 20 and the failure-direct-cause detecting circuit 210 then detects impact applied to the endoscope 20 to detect the pre-failure state in two steps of the fall detection and the impact detection, it is possible to obtain an effect in which an operation of an ordinary control of the endoscope 20 can be reduced from being erroneously detected as a state of falling or the like.

In a case in which an optical fiber 114 and/or a light converting member 116 (fluorescent substance) is damaged by the fall of the endoscope 20, it is possible to obtain an effect in which whether or not a failure of the optical fiber 114 and/or the light converting member 116 (fluorescent substance) occurs can be decided by examining the quantity of light of the return light from the light converting members 116 (fluorescent substances) in the failure detecting circuit 300.

It is possible to obtain an effect in which laser safety can be secured before a component of the endoscope 20 fails by changing, by the failure-direct-cause detecting circuit 210, the threshold value of the detection of the first pre-failure state based on magnitude of the impact detected by the impact sensor 212.

The memory 160 records that the endoscope 20 is impacted, thereby making it possible to obtain an effect in which the extent to which the endoscope 20 is impacted and the amount of damage accumulated in the endoscope 20 can be confirmed.

Third Embodiment (Configuration)

FIG. 13 shows function blocks of the endoscope system 10 according to the present embodiment. In FIG. 13, the members indicated by the same reference numerals as those shown in FIGS. 2 and 10 are the same members, and a detailed description thereof will be omitted. Hereinafter, different portions are mainly described. That is, portions that are not mentioned in the following description are the same as those of the first and second embodiments.

In the endoscope system 10, the endoscope 20 includes a cause predicting circuit 240 and a failure detecting circuit 300 as shown in FIG. 13.

<Cause Predicting Circuit 240>

The cause predicting circuit 240 includes an angular velocity sensor 272, which is an orbital displacement detector provided to a distal end of the insertion section 24 of the endoscope 20, a circular motion detecting circuit 274 configured to detect a circular motion of the distal end of the insertion section 24 of the endoscope 20 based on angular velocity detected by the angular velocity sensor 272, and a memory 276 storing a threshold value of a decision of the circular motion detection.

The angular velocity sensor 272 detects angular velocity of the distal end of the control section 22 and outputs a signal corresponding to the angular velocity to the circular motion detecting circuit 274. The circular motion detecting circuit 274 compares the output signal of the angular velocity sensor 272 with the threshold value stored in the memory 276. In a case in which the output signal of the angular velocity sensor 272 exceeds the threshold value, the circular motion detecting circuit 274 decides that the endoscope 20 is in the second pre-failure state before reaching the first pre-failure state. The second pre-failure state is, for example, a state in which the distal end of the insertion section 24 is performing the circular motion about the control section 22, not the normal movement of the insertion section 24. The state corresponds to, for example, a state in which the control section 22 is held by the hand and the distal end of the insertion section 24 moves like a pendulum. In a case in which the circular motion of the distal end of the insertion section 24 is fast, it is expected that a possibility that the insertion section 24 comes in contact with a wall or a near obstacle is high due to the movement like the pendulum.

In a case in which information on the detection of the second pre-failure state is input to the light source controller 150, the light source controller 150 reduces quantity of light of the light source 112 to quantity of light at a level with less influence on the human body. For example, the light source controller 150 reduces the quantity of light of the light source 112 to the quantity of light set to the class 2 or less of a safety reference of laser.

<Failure Detecting Circuit 300>

The failure detecting circuit 300 includes temperature sensors 322, which are heat detectors, provided on the peripheral of the optical fiber 114 and the light converting member 116, a heat generation decision circuit 324 configured to decide a heat generation of the optical fiber 114 and/or the light converting member 116 based on the temperature detected by the temperature sensors 322, and a memory 326 storing a threshold value of the decision of the heat generation detection.

The temperature sensors 322 are, for example, in the control section 22 and the insertion section 24 and are disposed, for example, at equal intervals along the optical fiber 114. In addition, at least one temperature sensor 322 may be additionally disposed in the vicinity of the light converting member 116. The temperature sensors 322 may be constituted of, for example, thermistors, thermocouples, or the like. The temperature sensors 322 detect the temperature of the optical fiber 114 and/or the light converting member 116 and output a signal according to the temperature to the heat generation decision circuit 324. In order to detect a temperature of each unit of the optical fiber 114, it is preferable that the temperature sensors 322 are disposed at a short interval along the optical fiber 114.

In a case in which the optical fiber 114 is folded or damaged, light is leaked from the folded position or the damaged position such that more heat than usual is generated. Similarly, in a case in which the light converting member 116 is damaged, light is leaked from the damaged position such that more heat than usual is generated. The heat generation decision circuit 324 compares the output signal of each temperature sensor 322 with the threshold value stored in the memory 326. The threshold value is set to a temperature that does not exceed in a state in which the failure does not occur in a state in which the quantity of light of the light source 112 is reduced. In a case in which the output signal of the temperature sensor 322 exceeds the threshold value, the heat generation decision circuit 324 decides that the optical fiber 114 or the light converting member 116 fails. The failure detecting circuit 300 outputs the decision result to the light source controller 150.

In a case in which the failure is not detected, the light source controller 150 returns the quantity of light of the light source 112 to normal quantity of light. On the contrary, in a case in which the failure is detected, the light source controller 150 stops the light source 112. In addition, the control device 30 warns that the illuminating system 110 has a failure and needs repair through the monitor 40 or the like.

The failure detecting circuit 300 may output information on an installation position of a temperature sensor 322 that exceeds the threshold value to the control device 30. This facilitates specifying failure positions.

(Action)

FIG. 14 shows an overall flow of a corresponding process of a case in which the distal end of an insertion section 24 of an endoscope 20 of the endoscope system 10 shown in FIG. 13 performs a circular motion. The present flow may be regularly performed during operation and use of the endoscope.

In a first step (3S1), the cause predicting circuit 240 decides whether or not the endoscope system 10 is in the second pre-failure state. In a case in which the distal end of the insertion section 24 of the endoscope 20 performs a motion such as a pendulum, the cause predicting circuit 240 detects the circular motion of the distal end of the insertion section 24 of the endoscope 20 based on the output of the angular velocity sensor 272 and decides that the endoscope 20 is in the second pre-failure state.

In a case in which the cause predicting circuit 240 does not detect the circular motion of the distal end of the insertion section 24 of the endoscope 20 and decides that the endoscope 20 is not in the second pre-failure state, the light source controller 150 does not particularly change an operation of the light source 112 and the endoscope system 10 is maintained in a state in which the endoscope system 10 can continue to be used as it is.

In a case in which the cause predicting circuit 240 detects the circular motion of the distal end of the endoscope 20 and decides that the endoscope 20 is in the second pre-failure state, in a next step (3S2), the light source controller 150 reduces the quantity of light of the light source 112.

Subsequently, in a next step (3S3), the failure detecting circuit 300 starts to decide whether or not the failure occurs in the illuminating system 110.

In a case in which the failure detecting circuit 300 decides that the failure occurs in the illuminating system 110, in a step (3S4), the light source controller 150 stops the light source 112. Additionally, the control device 30 may display a message prompting a user to perform the repair on the monitor 40. In addition, the control device 30 may prompt the user to perform the repair by issuing a warning sound.

In a case in which the failure detecting circuit 300 decides that the failure does not occur in the illuminating system 110, in a step (3S5), the light source controller 150 releases a limitation of the quantity of light of the light source 112 to return the light source 112.

(Effect)

Since the light source controller 150 reduces the quantity of light of the light source 112 based on information on the detection of the circular motion of the distal end of the insertion section 24 of the endoscope 20 by the cause predicting circuit 240, it is possible to obtain an effect in which laser light can be prevented from leaking at an unexpectedly high level.

The temperature sensors 322 detect the heat generation from the optical fiber 114 and/or the light converting member 116, such that whether or not the failure of the optical fiber 114 and/or the light converting member 116 occurs can be confirmed and the failure points may be specified.

Fourth Embodiment (Configuration)

Figure 15:
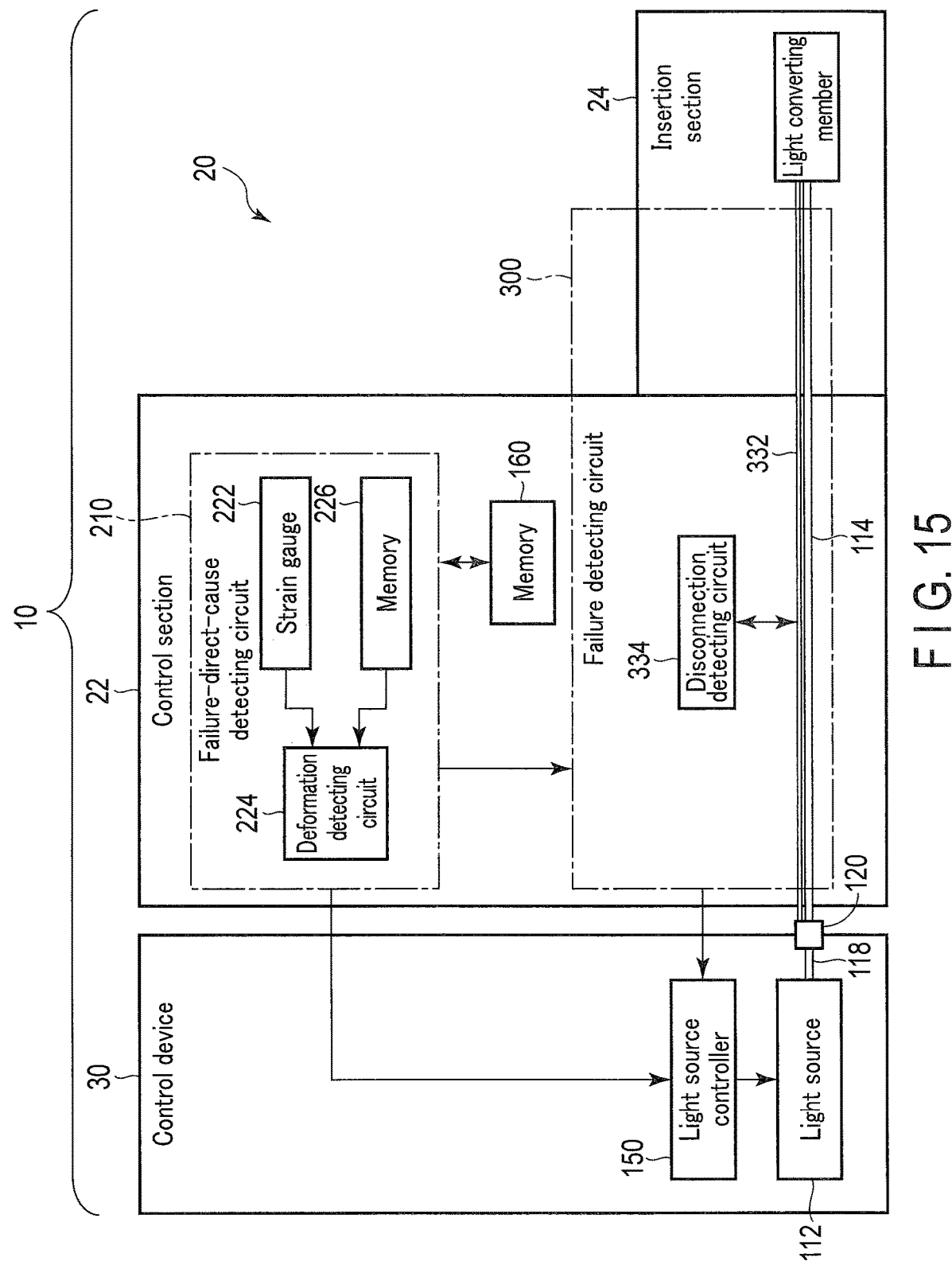
FIG. 15 shows function blocks of an endoscope system according to a fourth embodiment.

FIG. 15 shows function blocks of the endoscope system 10 according to the present embodiment. In FIG. 15, the members indicated by the same reference numerals as those shown in FIGS. 2 and 10 are the same members, and a detailed description thereof will be omitted. Hereinafter, different portions are mainly described. That is, portions that are not mentioned in the following description are the same as those of the first and second embodiments.

In the endoscope system 10, the endoscope 20 includes a failure-direct-cause detecting circuit 210 and a failure detecting circuit 300 as shown in FIG. 15.

<Failure-Direct-Cause Detecting Circuit 210>

The failure-direct-cause detecting circuit 210 includes a strain gauge 222, which is a deformation detector, provided in the endoscope 20, a deformation detecting circuit 224 configured to detect a deformation based on a strain detected by the strain gauge 222, and a memory 226 storing a threshold value of a decision of the deformation detection.

The strain gauge 222 is disposed on, for example, a hard section of the control section 22, for example, an exterior or interior substrate, for example, an electrical substrate or the like. The strain gauge 222 is preferably disposed at a position of the control section 22 that is most stressed and susceptible to deformation when the control section 22 falls down and then collides with the floor. Alternatively, the strain gauge 222 may be disposed at a portion at which the exterior of the control section 22 is susceptible to deformation, for example, at a thinner portion. The strain gauge 222 may be disposed at a portion that does not have bendability, such as the hard section of the insertion section 24 or a connector.

In addition, the strain gauge 222 may be provided to a position at which leakage of laser light is concerned when the illuminating system is damaged in the control section 22 or the insertion section 24, for example, on the periphery of the optical fiber 114, or on the periphery of the light converting member 116, or, in the case of a wireless type, on the periphery of the light source 112.

The strain gauge 222 detects the strain of the installation position of the endoscope 20 and outputs a signal corresponding to the strain to the deformation detecting circuit 224. The deformation detecting circuit 224 compares the output signal of the strain gauge 222 with the threshold value stored in the memory 226. When the output signal of the strain gauge 222 exceeds the threshold value, the deformation detecting circuit 224 decides that the endoscope 20 is in the first pre-failure state, which is a phenomenon of directly causing the failure of a component of the endoscope 20. The first pre-failure state is, for example, a state in which the endoscope 20 comes in contact with or collides with a wall or a floor, thereby causing the deformation of the endoscope 20. The failure-direct-cause detecting circuit 210 outputs the decision result, that is, detected information of the first pre-failure state to the light source controller 150.

In a case in which information on the detection of the first pre-failure state is input to the light source controller 150, the light source controller 150 stops the light source 112.

<Failure Detecting Circuit 300>

The failure detecting circuit 300 includes an electrical wire 332 extending side by side with the optical fiber 114 in the endoscope 20, that is, the control section 22 and the insertion section 24, and a disconnection detecting circuit 334 configured to detect a disconnection of the electrical wire 332. The electrical wire 332 is extremely weak in strength compared to the optical fiber 114 and is reliably disconnected when the optical fiber 114 is folded or damaged. It is desirable that the electrical wire is a single wire in order to facilitate detection of the disconnection. The disconnection detecting circuit 334 examines for example, whether or not energization is carried out between both ends of the electrical wire 332, and decides that the optical fiber 114 has failed in a case in which energization is not carried out.

In a case in which the failure is not detected, the light source controller 150 returns the quantity of light of the light source 112 to normal quantity of light. On the contrary, in a case in which the failure is detected, the control device 30 warns that the illuminating system 110 has a failure and needs repair through the monitor 40 or the like.

(Action)

FIG. 16 shows an overall flow of a corresponding process of a case in which the endoscope 20 of the endoscope system 10 shown in FIG. 15 reaches a first pre-failure state.

In a first step (4S1), the failure-direct-cause detecting circuit 210 decides whether or not the endoscope system 10 is in the first pre-failure state. Here, the first pre-failure state is, for example, a state in which the endoscope 20 is deformed.

In a case in which the failure-direct-cause detecting circuit 210 decides that the endoscope 20 is not in the first pre-failure state, the light source controller 150 does not particularly change an operation of the light source 112 and the endoscope system 10 is maintained in a state in which the endoscope system 10 can continue to be used as it is.

In a case in which the failure-direct-cause detecting circuit 210 decides that the endoscope 20 is in the first pre-failure state in which the endoscope 20 is deformed, in a next step (4S2), the light source controller 150 stops the light source 112.

Subsequently, in a next step (4S3), the failure detecting circuit 300 starts to decide whether or not the failure occurs in the illuminating system 110. Specifically, the disconnection detecting circuit 334 decides whether or not the electrical wire 332 is disconnected.

In a case in which the failure detecting circuit 300 decides that the failure occurs in the illuminating system 110, in a step (4S4), the control device 30 displays, for example, a message prompting the user to perform a repair on the monitor 40. In addition, the control device 30 may prompt the user to perform the repair by issuing a warning sound.

In a case in which the failure detecting circuit 300 decides that the failure does not occur in the illuminating system 110, in a step (4S5), the light source controller 150 again drives the light source 112 to return the light source 112. In addition, the memory 160 stores that the endoscope 20 reaches the first pre-failure state.

(Effect)

Since the light source controller 150 stops the light source 112 based on information on the detection of the deformation of the endoscope 20 by the failure-direct-cause detecting circuit 210, it is possible to obtain an effect in which laser light can be prevented from leaking at an unexpectedly high level. It is possible to detect the failure without influencing the generation of the illuminating light. In addition, since it is possible to decide the damaged position as the disconnection of the electrical wire by a decomposition examination at the time of a failure analysis, it is possible to obtain an effect in which it is easier to visually confirm the failure portion.

Whether or not the failure of the optical fiber 114 occurs can be confirmed by detecting, by the disconnection detecting circuit 334, a disconnection of the optical fiber 114 based on the disconnection of the electrical wire 332.

Application to Other Embodiments

The failure-direct-cause detecting circuit 210 including the strain gauge 222 according to the present embodiment may be used instead of the failure-direct-cause detecting circuit 210 including the impact sensor 212 according to the first embodiment. In addition, the failure detecting circuit 300 including the disconnection detecting circuit 334 according to the present embodiment may be used instead of the failure detecting circuit 300 including the optical coupler 302 or the light detector 306 according to the second embodiment and the failure detecting circuit 300 including the temperature sensors 322 according to the third embodiment.

Fifth Embodiment (Configuration)

FIG. 17 shows function blocks of the endoscope system 10 according to the present embodiment. In FIG. 17, the members indicated by the same reference numerals as those shown in FIGS. 2 and 10 are the same members, and a detailed description thereof will be omitted. Hereinafter, different portions are mainly described. That is, portions that are not mentioned in the following description are the same as those of the first and second embodiments.

In the endoscope system 10, the endoscope 20 includes a cause predicting circuit 240 and a failure detecting circuit 300 as shown in FIG. 13.

<Cause Predicting Circuit 240>

As the cause predicting circuit 240, the cause predicting circuit 240 described in the first and third embodiments may be used.

<Failure Detecting Circuit 300>

The failure detecting circuit 300 is the same as the failure detecting circuit 300 described in the fourth embodiment.

(Action)

Figure 18:
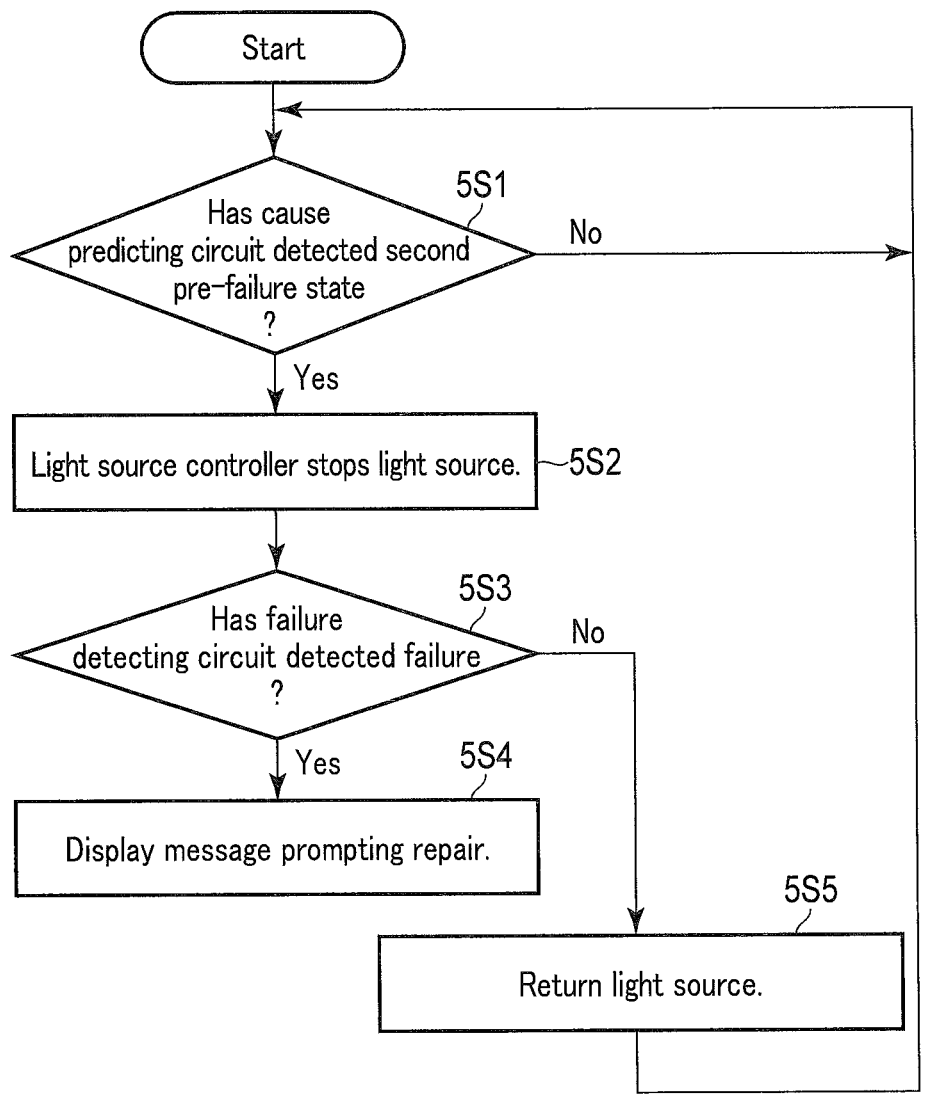
FIG. 18 shows an overall flow of a corresponding process of a case in which an endoscope of the endoscope system shown in FIG. 17 reaches a second pre-failure state.

FIG. 18 shows an overall flow of a corresponding process of a case in which an endoscope 20 of the endoscope system 10 shown in FIG. 17 reaches a second pre-failure state.

In a first step (5S1), the cause predicting circuit 240 decides whether or not the endoscope system 10 is in the second pre-failure state. Here, the second pre-failure state is, for example, a state in which the endoscope 20 is falling, a state in which the control section 22 is being thrown, or a state in which the distal end of the insertion section 24 is performing the circular motion.

In a case in which the cause predicting circuit 240 decides that the endoscope 20 is not in the second pre-failure state, the light source controller 150 does not particularly change an operation of the light source 112 and the endoscope system 10 is maintained in a state in which the endoscope system 10 can continue to be used as it is.

In a case in which the cause predicting circuit 240 decides that the endoscope 20 is in the second pre-failure state, in a next step (5S2), the light source controller 150 stops the light source 112.

Subsequently, in a next step (5S3), the failure detecting circuit 300 starts to decide whether or not the failure occurs in the illuminating system 110. Specifically, the disconnection detecting circuit 334 decides whether or not the electrical wire 332 is disconnected.

In a case in which the failure detecting circuit 300 decides that the failure occurs in the illuminating system 110, in a step (5S4), the control device 30 displays, for example, a message prompting the user to perform a repair on the monitor 40. In addition, the control device 30 may prompt the user to perform the repair by issuing a warning sound.

In a case in which the failure detecting circuit 300 decides that the failure does not occur in the illuminating system 110, in a step (5S5), the light source controller 150 again drives the light source 112 to return the light source 112. Such a situation can include, for example, a case in which the fall of the endoscope 20, the throwing of the control section 22, the separation of the control section 22 from the hand, or the like occurs, but the control section 22 is again caught by the operator before the collision.

(Effect)

Since the light source controller 150 stops the light source 112 before the endoscope 20 collides with an obstacle such as a floor or the like, based on information on a failure prediction of the endoscope 20 by the cause predicting circuit 240, safety of laser of the endoscope may be secured.

The failure detecting circuit, the failure-cause detecting circuit, and the failure-direct-cause detecting circuit and the cause predicting circuit constituting the failure-cause detecting circuit can be arbitrarily combined with the constitutions used in the respective embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
   an endoscope including a control section, an insertion section, and a light guide member;
   a light source configured to emit light to be guided by the light guide member;
   a failure-cause detecting circuit configured to detect a pre-failure state that causes a failure of the endoscope;
   a failure detecting circuit configured to detect the failure of the endoscope; and
   a light source controller configured to reduce a quantity of light of the light source according to the detection of the pre-failure state by the failure-cause detecting circuit, and stop the light source according to the detection of the failure by the failure detecting circuit.

2. The endoscope system according to claim 1, wherein the failure-cause detecting circuit includes a failure-direct-cause detecting circuit configured to detect a first pre-failure state that directly causes the failure of the endoscope.

3. The endoscope system according to claim 2,
   wherein circuit the failure-cause detecting circuit includes a cause predicting circuit configured to detect a second pre-failure state in which it is predicted that the endoscope reaches the first pre-failure state.

4. The endoscope system according to claim 3, wherein the cause predicting circuit includes an acceleration sensor configured to detect an acceleration applied to the endoscope, and
   the cause predicting circuit detects a fall of the endoscope as the second pre-failure state, based on the acceleration detected by the acceleration sensor.

5. The endoscope system according to claim 3, wherein the cause predicting circuit includes a velocity sensor configured to detect a velocity of the endoscope, and
   the cause predicting circuit detects a state in which the endoscope moves at a velocity of a predetermined value or more as the second pre-failure state, based on the velocity detected by the velocity sensor.

6. The endoscope system according to claim 3, wherein the cause predicting circuit includes an orbital displacement sensor configured to detect a circular motion of the insertion section, and
   the cause predicting circuit detects a state in which the insertion section is performing the circular motion as the second pre-failure state, based on a detection result of the orbital displacement sensor.

7. The endoscope system according to claim 3, wherein the cause predicting circuit includes a contact sensor configured to detect that the control section is held by a hand, and
   the cause predicting circuit detects a state in which the control section is not held by the hand for a time longer than a predetermined time as the second pre-failure state, based on a detection result of the contact sensor.

8. The endoscope system according to claim 3, further comprising a light converting member configured to convert the light guided by the light guide member into other light, the light converting member being mounted on the insertion section,
   wherein the failure detecting circuit includes a light detector configured to detect the light guided by the light guide member and reflected by the light converting member, or a heat detector configured to detect a heat generation from the light guide member and/or the light converting member.

9. The endoscope system according to claim 2, wherein the failure-direct-cause detecting circuit includes an impact sensor configured to detect impact applied to the endoscope, and
   the failure-direct-cause detecting circuit detects a state in which an impact of a predetermined value or more is applied to the endoscope as the first pre-failure state, based on a detection result of the impact sensor.

10. The endoscope system according to claim 9, wherein the failure-direct-cause detecting circuit changes a threshold value of the detection of the first pre-failure state based on magnitude of the impact detected by the impact sensor of the failure-direct-cause detecting circuit.

11. The endoscope system according to claim 9, further comprising a memory configured to store information on a detection result of the failure-direct-cause detecting circuit,
    wherein the failure-direct-cause detecting circuit changes a threshold value of the detection of the first pre-failure state, based on history information stored in the memory.

12. The endoscope system according to claim 2, wherein the failure-direct-cause detecting circuit includes a deformation sensor configured to detect a deformation of the endoscope, and
    the failure-direct-cause detecting circuit detects a state in which the deformation of the endoscope is a predetermined value or more as the first pre-failure state, based on a detection result of the deformation sensor.

13. The endoscope system according to claim 1, wherein the failure detecting circuit starts according to the detection of the pre-failure state by the failure-cause detecting circuit.

14. The endoscope system according to claim 1, wherein the light source controller stops the light source according to the detection of the pre-failure state by the failure-cause detecting circuit.

15. The endoscope system according to claim 1, wherein when the failure detecting circuit does not detect the failure after reducing the quantity of light of the light source or stopping the light source, the light source controller returns the quantity of light of the light source to the quantity of light prior to being reduced or stopping the light source.

16. The endoscope system according to claim 1, wherein the failure detecting circuit includes an electrical wire provided to extend side by side with the light guide member, and a disconnection detecting circuit configured to detect a disconnection of the electrical wire.

17. The endoscope system according to claim 1, wherein
the light source is disposed in the endoscope, and
the endoscope includes a transmitter configured to wirelessly transmit an image signal and a power supply configured to drive the endoscope.

18. The endoscope system according to claim 1, further comprising an endoscope controller configured to control the endoscope,
wherein the failure-cause detecting circuit is disposed on at least any one of the control section, the insertion section, a connector configured to connect the light source and the light guide member, and the endoscope controller.

\* \* \* \* \*